US005589380A

United States Patent [19]

Fasano et al.

[11] Patent Number: 5,589,380

[45] Date of Patent: Dec. 31, 1996

[54] **ISOLATED DNA MOLECULE ENCODING SHET1 OF *SHIGELLA FLEXNERI* 2A AND MUTANT *SHIGELLA FLEXNERI* 2A**

[75] Inventors: Alessio Fasano, Ellicott City; Myron M. Levine, Columbia; James P. Nataro, Catonsville; Fernando Noriega, Columbia, all of Md.

[73] Assignee: University of Maryland at Baltimore, Baltimore, Md.

[21] Appl. No.: 351,147

[22] Filed: Nov. 30, 1994

Related U.S. Application Data

[63] Continuation-in-part of Ser. No. 160,317, Dec. 2, 1993, Pat. No. 5,468,639, which is a continuation-in-part of Ser. No. 894,774, Jun. 5, 1992, abandoned.

[51] Int. Cl.[6] .............................. C12N 1/20; C12P 21/04; C07K 1/00; C07H 19/00

[52] U.S. Cl. .................... 435/252.3; 435/71.1; 435/71.3; 435/252.1; 435/320.1; 530/350; 530/825; 536/22.1; 536/23.1; 536/23.7

[58] Field of Search ................................. 435/71.1, 71.3, 435/252.1, 320.1; 530/350, 825; 536/22.1, 23.1, 23.7

[56] References Cited

U.S. PATENT DOCUMENTS 5,204,097 4/1993 Arnon et al. .

OTHER PUBLICATIONS

Noriega F R; Fasano A; Formal S; Maneval D; Lioa J; Chanasongcram S; Levine M M, "Cloning and regulation of the gene encoding for a chromosomally encoded enterotoxin in *Shigella flexneri*2a (SHET1)" 34th Interscience Conference on Antimicrobial Agents and Chemotherapy, Orlando, Florida, USA, Oct. 4–7, 1994. Abstracts of the Interscience Conference on Antimicrobial Agents andChemotherapy 34(0). 1994. 63.

Fasano et al, *J. Pediatr. Gastroenterol. Nutr.*, 13:320 (1991).

Fasano et al, *Infect. Immun.*, 58(11):3717–3723 (1990).

Maurer et al, *Methods in Enzymology*, 70:49–70 (1980).

Strockbine et al, *Infec. Immun.*, 50(3):695–700 (1985).

Levine, *J. Inf. Dis.*, 155(3):377–389 (1987).

Fasano et al, "Elaboration of an Enterotoxin by *Shigella Flexneria* 2a", *Rivista Italian Di Pediatria*, 17(4):182 (Abstract) (Aug., 1991).

Lecture Slides, "Production by Enteroinvasive *E. coli* and *Shigella Flexneria* 2a of a Novel Enterotoxin Moiety", presented at Walter Reed Army Institute, Apr. 15, 1990.

Fasano et al, "Enterotoxic Factors by *Shigella Flexneria* 2a", presented at the *29th U.S.-Japan Joint Conference on Cholera and Related Diarrheal Diseases*, Dec. 2, 1992.

Nataro et al, "Cloning and Sequencing of a New Plasmid–Encoded Enterotoxin in Enteroinvasive *E. coli* and *Shigella*", presented at the *29th U.S.-Japan Joint Conference on Chlorera and Related Diarrheal Diseases*, Dec. 2, 1992.

Noriega et al, "Construction and Characterization of Oral Attenuated Shigella Vaccine–Candidates and their Potential Use as Live Vector–Hyrbrid Vaccines", presented at the *29th U.S.-Joint Conferences on Cholera and Related Diarrheal Diseases*, Dec. 2, 1992.

Glover, "Principles of Cloning DNA" *Gene Cloning*, pp. 1–20 (1984).

Lee et al, "Generation of cDNA Probes Directed by Amino Acid Sequence: Cloning of Urate Oxidase", *Science*, 239:1288–1291 (1988).

*Primary Examiner*—Charles L. Patterson, Jr.
*Assistant Examiner*—Hyosuk Kim
*Attorney, Agent, or Firm*—Sughrue, Mion, Zinn, Macpeak & Seas

[57] ABSTRACT

Substantially pure enterotoxins of *Shigella flexneri* 2a are described, along with a method for obtaining the same, antibodies having binding specificity to the enterotoxins and a method for use of the enterotoxins to develop a non-reactogenic *Shigella flexneri* 2a vaccine candidate.

8 Claims, 15 Drawing Sheets

FIGURE 6A

```
ATCGATATAT TGTTTATTGT CAGTATGGCT CAATGTGATA                40

ATAGTTGGAA AGTTTGATGG GTTTCGCCCC GTTGTAGCGG                80

TAGTCGACCC CGTTGTAGCG GTAGTCGAGC TGGAAGGTCT               120

TCAGGCACTG CTTACAGCGA TAGAGCAGCC CCCCAGAACT               160

GGAATGGCCG TTCCGATACC CCCCTGAGTT TCAGAGTAAC               200

GGGGACAAAC CACATCAATC TTTGCCATCA ATCATCCAAA               240

GGGCAAAGAG TACAACAACA CTAAGTCTGC GTCACAACCC               280

ATCAATGAAA GGAATATATA CAT ATG CCA TCA GTA ATT             318
                              Met Pro Ser Val Asn
                               1               5

TTA ATC CCA TCA AGG AAA ATA TGT TTG CAA AAT ATG           354
Leu Ile Pro Ser Arg Lys Ile Cys Leu Gln Asn Met
                 10                  15

ATA AAT AAA GAC AAC GTC TCT GTT GAG ACA ATC CAG           390
Ile Asn Lys Asp Asn Val Ser Val Glu Thr Ile Gln
         20                  25

TCT CTA TTG CAC TCA AAA CAA TTG CCA TAT TTT TCT           426
Ser Leu Leu His Ser Lys Gln Leu Pro Tyr Phe Ser
 30                  35                  40

GAC AAG AGG AGT TTT TTA TTA AAT CTA AAT TGC CAA           462
Asp Lys Arg Ser Phe Leu Leu Asn Leu Asn Cys Gln
             45                  50

GTT ACC GAT CAC TCT GGA AGA CTT ATT GTC TGT CGA           498
Val Thr Asp His Ser Gly Arg Leu Ile Val Cys Arg
     55                  60                  65

CAT TTA GCT TCC TAC TGG ATA GCA CAG TTT AAC AAA           534
His Leu Ala Ser Tyr Trp Ile Ala Gln Phe Asn Lys
                 70                  75

AGT AGT GGT CAC GTG GAT TAT CAT CAC TTT GCT TTT           570
Ser Ser Gly His Val Asp Tyr His His Phe Ala Phe
         80                  85

CCG GAT GAA ATT AAA AAT TAT GTT TCA GTG AGT GAA           606
Pro Asp Glu Ile Lys Asn Tyr Val Ser Val Ser Glu
 90                  95                 100
```

FIGURE 6B

| | | | | | | | | | | | | |
|---|---|---|---|---|---|---|---|---|---|---|---|---|
| GAA | GAA | AAG | GCT | ATT | AAT | GTG | CCT | GCT | ATT | ATT | TAT | 642 |
| Glu | Glu | Lys | Ala | Ile | Asn | Val | Pro | Ala | Ile | Ile | Tyr | |
| | | | 105 | | | | | 110 | | | | |
| TTT | GTT | GAA | AAC | GGT | TCA | TGG | GGA | GAT | ATT | ATT | TTT | 678 |
| Phe | Val | Glu | Asn | Gly | Ser | Trp | Gly | Asp | Ile | Ile | Phe | |
| | 115 | | | | | 120 | | | | | 125 | |
| TAT | ATT | TTC | AAT | GAA | ATG | ATT | TTT | CAT | TCC | GAA | AAA | 714 |
| Tyr | Ile | Phe | Asn | Glu | Met | Ile | Phe | His | Ser | Glu | Lys | |
| | | | | 130 | | | | | 135 | | | |
| AGC | AGA | GCA | CTA | GAA | ATA | AGT | ACA | TCA | AAT | CAC | AAT | 750 |
| Ser | Arg | Ala | Leu | Glu | Ile | Ser | Thr | Ser | Asn | His | Asn | |
| | | 140 | | | | | 145 | | | | | |
| ATG | GCA | TTA | GGC | TTG | AAG | ATT | AAA | GAA | ACT | AAA | AAT | 786 |
| Met | Ala | Leu | Gly | Leu | Lys | Ile | Lys | Glu | Thr | Lys | Asn | |
| 150 | | | | | 155 | | | | | 160 | | |
| GGG | GGG | GAT | TTT | GTC | ATT | CAG | CTT | TAT | GAT | CCC | AAC | 822 |
| Gly | Gly | Asp | Phe | Val | Ile | Gln | Leu | Tyr | Asp | Pro | Asn | |
| | | | 165 | | | | | 170 | | | | |
| CAT | ACA | GCA | ACT | CAT | TTA | CGA | GCA | GAG | TTT | AAC | AAA | 858 |
| His | Thr | Ala | Thr | His | Leu | Arg | Ala | Glu | Phe | Asn | Lys | |
| | 175 | | | | | 180 | | | | | 185 | |
| TTT | AAC | TTA | GCT | AAA | ATA | AAA | AAA | CTG | ACT | GTA | GAT | 894 |
| Phe | Asn | Leu | Ala | Lys | Ile | Lys | Lys | Leu | Thr | Val | Asp | |
| | | | | 190 | | | | | 195 | | | |
| AAT | TTT | CTT | GAT | GAA | AAA | CAT | CAG | AAA | TGT | TAT | GGT | 930 |
| Asn | Phe | Leu | Asp | Glu | Lys | His | Gln | Lys | Cys | Tyr | Gly | |
| | | 200 | | | | | 205 | | | | | |
| CTT | ATA | TCC | GAC | GGT | ATG | TCT | ATA | TTT | GTG | GAC | AGA | 966 |
| Leu | Ile | Ser | Asp | Gly | Met | Ser | Ile | Phe | Val | Asp | Arg | |
| 210 | | | | | 215 | | | | | 220 | | |
| CAT | ACT | CCA | ACA | AGC | ATG | TCC | TCC | ATA | ATC | AGA | TGG | 1002 |
| His | Thr | Pro | Thr | Ser | Met | Ser | Ser | Ile | Ile | Arg | Trp | |
| | | | 225 | | | | | 230 | | | | |
| CCT | AAT | AAT | TTA | CTT | CAC | CCC | AAA | GTT | ATT | TAT | CAC | 1038 |
| Pro | Asn | Asn | Leu | Leu | His | Pro | Lys | Val | Ile | Tyr | His | |
| | 235 | | | | | 240 | | | | | 245 | |
| GCG | ATG | CGT | ATG | GGA | TTG | ACT | GAG | CTA | ATC | CAA | AAA | 1074 |
| Ala | Met | Arg | Met | Gly | Leu | Thr | Glu | Leu | Ile | Gln | Lys | |
| | | | | 250 | | | | | 255 | | | |

FIGURE 6C

```
GTA ACA AGA GTC GTA CAA CTA TCT GAC CTT TCA GAC  1110
Val Thr Arg Val Val Gln Leu Ser Asp Leu Ser Asp
        260                 265

AAT ACG TTA GAA TTA CTT TTG GCA GCC AAA AAT GAC  1146
Asn Thr Leu Glu Leu Leu Leu Ala Ala Lys Asn Asp
270                 275                 280

GAT GGT TTG TCA GGA TTG CTT TTA GCT TTA CAA AAT  1182
Asp Gly Leu Ser Gly Leu Leu Leu Ala Leu Gln Asn
            285                 290

GGG CAT TCA GAT ACA ATC TTA GCA TAC GGA GAA CTC  1218
Gly His Ser Asp Thr Ile Leu Ala Tyr Gly Glu Leu
    295                 300                 305

CTG GAA ACT TCT GGA CTT AAC CTT GAT AAA ACG GTA  1254
Leu Glu Thr Ser Gly Leu Asn Leu Asp Lys Thr Val
                310                 315

GAA CTA CTA ACT GCG GAA GGA ATG GGA GGA CGA ATA  1290
Glu Leu Leu Thr Ala Glu Gly Met Gly Gly Arg Ile
        320                 325

TCG GGT TTA TCC CAA GCA CTT CAA AAT GGG CAT GCA  1326
Ser Gly Leu Ser Gln Ala Leu Gln Asn Gly His Ala
330                 335                 340

GAA ACT ATC AAA ACA TAC GGA AGG CTT CTC AAG AAG  1362
Glu Thr Ile Lys Thr Tyr Gly Arg Leu Leu Lys Lys
            345                 350

AGA GCA ATA AAT ATC GAA TAC AAT AAG CTG AAA AAT  1398
Arg Ala Ile Asn Ile Glu Tyr Asn Lys Leu Lys Asn
    355                 360                 365

TTG CTG ACC GCT TAT TAT TAT GAT GAA GTA CAC AGA  1434
Leu Leu Thr Ala Tyr Tyr Tyr Asp Glu Val His Arg
                370                 375

CAG ATA CCT GGA CTA ATG TTT GCT CTT CAA AAT GGA  1470
Gln Ile Pro Gly Leu Met Phe Ala Leu Gln Asn Gly
        380                 385

CAT GCA GAT GCT ATA CGC GCA TAC GGT GAG CTC ATT  1506
His Ala Asp Ala Ile Arg Ala Tyr Gly Glu Leu Ile
390                 395                 400

CTT AGC CCC CCT CTC CTC AAC TCA GAG GAT ATT GTA  1542
Leu Ser Pro Pro Leu Leu Asn Ser Glu Asp Ile Val
            405                 410
```

FIGURE 6D

```
AAT TTG CTG GCC TCA AGG AGA TAT GAC AAT GTT CCC   1578
Asn Leu Leu Ala Ser Arg Arg Tyr Asp Asn Val Pro
    415                 420                 425

GGA CTT CTG TTA GCA TTG AAT AAT GGA CAG GCT GAT   1614
Gly Leu Leu Leu Ala Leu Asn Asn Gly Gln Ala Asp
                430                 435

GCA ATC TTA GCT TAT GGT GAT ATC TTG AAT GAG GCA   1650
Ala Ile Leu Ala Tyr Gly Asp Ile Leu Asn Glu Ala
        440                 445

AAA CTT AAC TTG GAT AAA AAA GCA GAG CTG TTA GAA   1686
Lys Leu Asn Leu Asp Lys Lys Ala Glu Leu Leu Glu
450                 455                 460

GCG AAA GAT TCT AAT GGT TTA TCT GGA TTG TTT GTA   1722
Ala Lys Asp Ser Asn Gly Leu Ser Gly Leu Phe Val
            465                 470

GCC TTG CAT AAT GGA TGT GTA GAA ACA ATT ATT GCT   1758
Ala Leu His Asn Gly Cys Val Glu Thr Ile Ile Ala
    475                 480                 485

TAT GGG AAA ATA CTT CAC ACT GCA GAC CTT ACT CCA   1794
Tyr Gly Lys Ile Leu His Thr Ala Asp Leu Thr Pro
                490                 495

CAT CAG GCA TCA AAA TTA CTG GCA GCA GAA GGC CCA   1830
His Gln Ala Ser Lys Leu Leu Ala Ala Glu Gly Pro
        500                 505

AAT GGG GTA TCT GGA TTA ATT ATA GCT TTT CAA AAT   1866
Asn Gly Val Ser Gly Leu Ile Ile Ala Phe Gln Asn
510                 515                 520

AGG AAT TTT GAG GCA ATA AAA ACT TAT ATG GGA ATA   1902
Arg Asn Phe Glu Ala Ile Lys Thr Tyr Met Gly Ile
            525                 530

ATA AAA AAT GAA AAT ATT ACA CCT GAA GAA ATA GCA   1938
Ile Lys Asn Glu Asn Ile Thr Pro Glu Glu Ile Ala
    535                 540                 545

GAA CAC TTG GAC AAA AAA AAT GGA AGT GAT TTT CTA   1974
Glu His Leu Asp Lys Lys Asn Gly Ser Asp Phe Leu
                550                 555

GAA ATT ATG AAG AAT ATA AAA AGC TGAATATTAT        2008
Glu Ile Met Lys Asn Ile Lys Ser
        560                 565
```

FIGURE 7A

ACCCATCAAT GAAAGGAATA TATA CAT ATG CCA TCA GTA 39
Met Pro Ser Val
1

AAT TTA ATC CCA TCA AGG AAA ATA TGT TTG CAA AAT 75
Asn Leu Ile Pro Ser Arg Lys Ile Cys Leu Gln Asn
5 10 15

ATG ATA AAT AAA GAC AAC GTC TCT GTT GAG ACA ATC 111
Met Ile Asn Lys Asp Asn Val Ser Val Glu Thr Ile
20 25

CAG TCT CTA TTG CAC TCA AAA CAA TTG CCA TAT TTT 147
Gln Ser Leu Leu His Ser Lys Gln Leu Pro Tyr Phe
30 35 40

TCT GAC AAG AGG AGT TTT TTA TTA AAT CTA AAT TGC 183
Ser Asp Lys Arg Ser Phe Leu Leu Asn Leu Asn Cys
45 50

CAA GTT ACC GAT CAC TCT GGA AGA CTT ATT GTC TGT 219
Gln Val Thr Asp His Ser Gly Arg Leu Ile Val Cys
55 60

CGA CAT TTA GCT TCC TAC TGG ATA GCA CAG TTT AAC 255
Arg His Leu Ala Ser Tyr Trp Ile Ala Gln Phe Asn
65 70 75

AAA AGT AGT GGT CAC GTG GAT TAT CAT CAC TTT GCT 291
Lys Ser Ser Gly His Val Asp Tyr His His Phe Ala
80 85

TTT CCG GAT GAA ATT AAA AAT TAT GTT TCA GTG AGT 327
Phe Pro Asp Glu Ile Lys Asn Tyr Val Ser Val Ser
90 95 100

GAA GAA GAA AAG GCT ATT AAT GTG CCT GCT ATT ATT 363
Glu Glu Glu Lys Ala Ile Asn Val Pro Ala Ile Ile
105 110

TAT TTT GTT GAA AAC GGT TCA TGG GGA GAT ATT ATT 399
Tyr Phe Val Glu Asn Gly Ser Trp Gly Asp Ile Ile
115 120

TTT TAT ATT TTC AAT GAA ATG ATT TTT CAT TCC GAA 435
Phe Tyr Ile Phe Asn Glu Met Ile Phe His Ser Glu
125 130 135

AAA AGC AGA GCA CTA GAA ATA AGT ACA TCA AAT CAC 471
Lys Ser Arg Ala Leu Glu Ile Ser Thr Ser Asn His
140 145

FIGURE 7B

```
AAT ATG GCA TTA GGC TTG AAG ATT AAA GAA ACT AAA    507
Asn Met Ala Leu Gly Leu Lys Ile Lys Glu Thr Lys
    150                 155                 160

AAT GGG GGG GAT TTT GTC ATT CAG CTT TAT GAT CCC    543
Asn Gly Gly Asp Phe Val Ile Gln Leu Tyr Asp Pro
                165                 170

AAC CAT ACA GCA ACT CAT TTA CGA GCA GAG TTT AAC    579
Asn His Thr Ala Thr His Leu Arg Ala Glu Phe Asn
        175                 180

AAA TTT AAC TTA GCT AAA ATA AAA AAA CTG ACT GTA    615
Lys Phe Asn Leu Ala Lys Ile Lys Lys Leu Thr Val
185                 190                 195

GAT AAT TTT CTT GAT GAA AAA CAT CAG AAA TGT TAT    651
Asp Asn Phe Leu Asp Glu Lys His Gln Lys Cys Tyr
            200                 205

GGT CTT ATA TCC GAC GGT ATG TCT ATA TTT GTG GAC    687
Gly Leu Ile Ser Asp Gly Met Ser Ile Phe Val Asp
    210                 215                 220

AGA CAT ACT CCA ACA AGC ATG TCC TCC ATA ATC AGA    723
Arg His Thr Pro Thr Ser Met Ser Ser Ile Ile Arg
                225                 230

TGG CCT GAT AAT TTA CTT CAC CCC AAA GTT ATT TAT    759
Trp Pro Asp Asn Leu Leu His Pro Lys Val Ile Tyr
        235                 240

CAC GCG ATG CGT ATG GGA TTG ACT GAG CTA ATC CAA    795
His Ala Met Arg Met Gly Leu Thr Glu Leu Ile Gln
245                 250                 255

AAA GTA ACA AGA GTC GTA CAA CTA TCT GAC CTT TCA    831
Lys Val Thr Arg Val Val Gln Leu Ser Asp Leu Ser
            260                 265

GAC AAT ACG TTA GAA TTA CTT TTG GCA GCC AAA AAT    867
Asp Asn Thr Leu Glu Leu Leu Leu Ala Ala Lys Asn
    270                 275                 280

GAC GAT GGT TTG TCA GGA TTG CTT TTA GCT TTA CAA    903
Asp Asp Gly Leu Ser Gly Leu Leu Leu Ala Leu Gln
                285                 290

AAT GGG CAT TCA GAT ACA ATC TTA GCA TAC GGA GAA    939
Asn Gly His Ser Asp Thr Ile Leu Ala Tyr Gly Glu
        295                 300
```

FIGURE 7C

CTC TTG GAA ACT TCT GGA CTT AAC CTT GAT AAA ACG 975
Leu Leu Glu Thr Ser Gly Leu Asn Leu Asp Lys Thr
305 310 315

GTA GAA CTA CTA ACT GCG GAA GGA ATG GGA GGA CGA 1011
Val Glu Leu Leu Thr Ala Glu Gly Met Gly Gly Arg
320 325

ATA TCG GGT TTA TCC CAA GCA CTT CAA AAT GGG CAT 1047
Ile Ser Gly Leu Ser Gln Ala Leu Gln Asn Gly His
330 335 340

GCA GAA ACT ATC AAA ACA TAC GGA AGG CTT CTC AAG 1083
Ala Glu Thr Ile Lys Thr Tyr Gly Arg Leu Leu Lys
345 350

AAG AGA GCA ATA AAT ATC GAA TAC AAT AAG CTG AAA 1119
Lys Arg Ala Ile Asn Ile Glu Tyr Asn Lys Leu Lys
355 360

AAT TTG CTG ACC GCT TAT TAT TAT GAT GAA GTA CAC 1155
Asn Leu Leu Thr Ala Tyr Tyr Tyr Asp Glu Val His
365 370 375

AGA CAG ATA CCC GGA CTA ATG TTT GCT CTT CAA AAT 1191
Arg Gln Ile Pro Gly Leu Met Phe Ala Leu Gln Asn
380 385

GGA CAT GCA GAT GCT ATA CGC GCA TAC GGT GAG CTC 1227
Gly His Ala Asp Ala Ile Arg Ala Tyr Gly Glu Leu
390 395 400

ATT CTT AGC CCC CCT CTC CTC AAC TCA GAG GAT ATT 1263
Ile Leu Ser Pro Pro Leu Leu Asn Ser Glu Asp Ile
405 410

GTA AAT TTG CTG GCC TCA AGG AGA TAT GAC AAT GTT 1299
Val Asn Leu Leu Ala Ser Arg Arg Tyr Asp Asn Val
415 420

CCC GGA CTT CTG TTA GCA TTG AAT AAT GGA CAG GCT 1335
Pro Gly Leu Leu Leu Ala Leu Asn Asn Gly Gln Ala
425 430 435

GAT GCA ATC TTA GCT TAT GGT GAT ATC TTG AAT GAG 1371
Asp Ala Ile Leu Ala Tyr Gly Asp Ile Leu Asn Glu
440 445

GCA AAA CTT AAC TTG GAT AAA AAA GCA GAG CTG TTA 1407
Ala Lys Leu Asn Leu Asp Lys Lys Ala Glu Leu Leu
450 455 460

FIGURE 7D

GAA GCG AAA GAT TCT AAT GGT TTA TCT GGA TTG TTT 1443
Glu Ala Lys Asp Ser Asn Gly Leu Ser Gly Leu Phe
465 470

GTA GCC TTG CAT AAT GGA TGT GTA GAA ACA ATT ATT 1479
Val Ala Leu His Asn Gly Cys Val Glu Thr Ile Ile
475 480

GCT TAT GGG AAA ATA CTT CAC ACT GCA GAC CTT ACT 1515
Ala Tyr Gly Lys Ile Leu His Thr Ala Asp Leu Thr
485 490 495

CCA CAT CAG GCA TCA AAA TTA CTG GCA GCA GAA GGC 1551
Pro His Gln Ala Ser Lys Leu Leu Ala Ala Glu Gly
500 505

CCA AAT GGG GTA TCT GGA TTA ATT ATA GCT TTT CAA 1587
Pro Asn Gly Val Ser Gly Leu Ile Ile Ala Phe Gln
510 515 520

AAT AGG AAT TTT GAG GCA ATA AAA ACT TAT ATG AAA 1623
Asn Arg Asn Phe Glu Ala Ile Lys Thr Tyr Met Lys
525 530

ATA ATA AAA AAT GAA AAT ATT ACA CCT GAA GAA ATA 1659
Ile Ile Lys Asn Glu Asn Ile Thr Pro Glu Glu Ile
535 540

GCA GAA CAC TTG GAC AAA AAA AAT GGA AGT GAT TTT 1695
Ala Glu His Leu Asp Lys Lys Asn Gly Ser Asp Phe
545 550 555

CTA GAA ATT ATG AAG AAT ATA AAA AGC 1722
Leu Glu Ile Met Lys Asn Ile Lys Ser
560 565

FIGURE 9A

| | | | | | | | | | | | | |
|---|---|---|---|---|---|---|---|---|---|---|---|---|
| ATG | GTT | CAG | CGT | AAT | ATT | CCC | TTC | ATA | CTG | GCT | CCT | 36 |
| Met | Val | Gln | Arg | Asn | Ile | Pro | Phe | Ile | Leu | Ala | Pro | |
| 1 | | | | 5 | | | | | 10 | | | |
| GTC | ATT | CAC | GGT | GTC | CGG | GAC | AGA | GGT | ACC | TTC | CTC | 72 |
| Val | Ile | His | Gly | Val | Arg | Asp | Arg | Gly | Thr | Phe | Leu | |
| | | 15 | | | | | 20 | | | | | |
| CGG | AAT | GAC | ATA | ATT | TCC | TGT | TCC | GTC | ATT | TTT | ATC | 108 |
| Arg | Asn | Asp | Ile | Ile | Ser | Cys | Ser | Val | Ile | Phe | Ile | |
| 25 | | | | | 30 | | | | | 35 | | |
| CAC | AAA | TGC | CCT | GTC | ACT | TCC | CAG | TGT | GAT | ATG | GCT | 144 |
| His | Lys | Cys | Pro | Val | Thr | Ser | Gln | Cys | Asp | Met | Ala | |
| | | | 40 | | | | | 45 | | | | |
| GTT | ATC | CGA | CTT | AAT | GTC | ACT | GTT | CAG | CGA | GGC | GTT | 180 |
| Val | Ile | Arg | Leu | Asn | Val | Thr | Val | Gln | Arg | Gly | Val | |
| | 50 | | | | | 55 | | | | | 60 | |
| ACG | TGA | AAG | ATG | GAA | GTC | AGC | GTC | TTT | CAG | CGA | CAG | 216 |
| Thr | * | Lys | Met | Glu | Val | Ser | Val | Phe | Gln | Arg | Gln | |
| | | | | 65 | | | | | 70 | | | |
| TGT | TTT | CAT | TGT | AAA | CTG | ACG | GTT | TTC | CCA | GTC | TTT | 252 |
| Cys | Phe | His | Cys | Lys | Leu | Thr | Val | Phe | Pro | Val | Phe | |
| | | 75 | | | | | 80 | | | | | |
| CTG | GTT | CAG | GCT | GAC | CGG | TGC | ACT | GCC | ACT | GAT | GGA | 288 |
| Leu | Val | Gln | Ala | Asp | Arg | Cys | Thr | Ala | Thr | Asp | Gly | |
| 85 | | | | | 90 | | | | | 95 | | |
| GGC | ATG | GAT | AAC | CGG | ATG | TCC | CTG | GAA | TAT | CAG | GGT | 324 |
| Gly | Met | Asp | Asn | Arg | Met | Ser | Leu | Glu | Tyr | Gln | Gly | |
| | | | 100 | | | | | 105 | | | | |
| GCC | ACT | GTC | CTG | ACT | CAG | GGT | ACC | TTC | CGG | CAG | GTT | 360 |
| Ala | Thr | Val | Leu | Thr | Gln | Gly | Thr | Phe | Arg | Gln | Val | |
| | 110 | | | | | 115 | | | | | 120 | |
| CAC | GCT | ACC | ATC | AAA | GAT | TAC | CTT | TCT | TCC | CCC | CGG | 396 |
| His | Ala | Thr | Ile | Lys | Asp | Try | Leu | Ser | Ser | Pro | Arg | |
| | | | | 125 | | | | | 130 | | | |
| CAC | CTG | TGG | AAT | GGC | GAC | ATC | CAT | ATT | CCC | GGT | CAG | 432 |
| His | Leu | Trp | Asn | Gly | Asp | Ile | His | Ile | Pro | Gly | Gln | |
| | | 135 | | | | | 140 | | | | | |
| CTG | ACC | ATG | AAA | GAT | AAC | GGG | TTG | TTT | TGC | CCG | CCC | 468 |
| Leu | Thr | Met | Lys | Asp | Asn | Gly | Leu | Phe | Cys | Pro | Pro | |
| 145 | | | | | 150 | | | | | 155 | | |

FIGURE 9B

| | | | | | | | | | | | | |
|---|---|---|---|---|---|---|---|---|---|---|---|---|
| GGC | CAG | GAT | CCT | ATC | TTT | TAC | TGT | CTG | AAC | TGC | TTT | 504 |
| Gly | Gln | Asp | Pro | Ile | Phe | Tyr | Cys | Leu | Asn | Cys | Val | |
| | | | 160 | | | | | 165 | | | | |
| GTT | TTT | GTT | CAT | GCC | AAC | AAA | CTC | CCA | CTG | AGC | CGG | 540 |
| Val | Phe | Val | His | Ala | Asn | Lys | Leu | Pro | Leu | Ser | Arg | |
| | 170 | | | | | 175 | | | | | 180 | |
| ATC | ATT | CAG | GCT | GTT | CCC | CCA | CAG | AGT | GTT | ACC | ATA | 576 |
| Ile | Ile | Gln | Ala | Val | Pro | Pro | Gln | Ser | Val | Thr | Ile | |
| | | | | 185 | | | | | 190 | | | |
| GCT | GGC | AGA | TTT | CAG | AAT | ATA | GAA | GCG | GGT | CTG | GCT | 612 |
| Ala | Gly | Arg | Phe | Gln | Asn | Ile | Glu | Ala | Gly | Leu | Ala | |
| | | 195 | | | | | 200 | | | | | |
| GTT | GAG | TAT | CAT | GCT | GTA | CAG | GTT | TCC | TGG | AGT | GCC | 648 |
| Val | Glu | Tyr | His | Ala | Val | Gln | Val | Ser | Trp | Ser | Ala | |
| 205 | | | | | 210 | | | | | 215 | | |
| GGT | ACC | ACC | AAA | GGG | GGA | TAT | ATT | TCC | AAT | CGT | CGG | 684 |
| Gly | Thr | Thr | Lys | Gly | Gly | Tyr | Ile | Ser | Asn | Arg | Arg | |
| | | | 220 | | | | | 225 | | | | |
| TTC | ACT | GAC | ATT | TGT | ATC | CTG | AGC | CTT | AAG | ATC | CAG | 720 |
| Phe | Thr | Asp | Ile | Cys | Ile | Leu | Ser | Leu | Lys | Ile | Gln | |
| | 230 | | | | | 235 | | | | | 240 | |
| TAA | | | | | | | | | | | | |
| * | | | | | | | | | | | | 723 |

ISOLATED DNA MOLECULE ENCODING SHET1 OF *SHIGELLA FLEXNERI* 2A AND MUTANT *SHIGELLA FLEXNERI* 2A

CROSS-REFERENCE TO RELATED APPLICATIONS

This is a Continuation-in-part of U.S. patent application Ser. No. 08/160,317, filed Dec. 2, 1993, now U.S. Pat. No. 5,468,639, which in turn is a Continuation-in-part of U.S. patent application Ser. No. 07/894,774, filed Jun. 5, 1992, now abandoned.

FIELD OF THE INVENTION

The present invention relates to two substantially pure enterotoxins of *Shigella flexneri* 2*a* (hereinafter "SheT1" and "ShET2"), a method for obtaining the same, antibodies having binding specificity to the enterotoxins and a method for use of the enterotoxins to develop a non-reactogenic *Shigella flexneri* 2*a* vaccine candidate.

BACKGROUND OF THE INVENTION

Much has been written about the molecular pathogenesis of Shigella with respect to the genes and gene products involved in their ability to invade epithelial cells, and thereby to cause dysentery (Makino et al, *Microb. Pathog.*, 5:267–274 (1988); Sansonetti et al, *Infect. Immun.*, 35:852–860 (1982); Hale et al, *Infect. Immun.*, 40:340–350 (1983); Pal et al, *J. Clin. Microbiol.*, 27:561–563 (1989); and Venkatesan et al, *Proc. Nat'l. Acad. Sci. U.S.A.*, 85:9317–9321 (1988)). In contrast, surprisingly little is known of the precise mechanisms by which Shigella cause watery diarrhea.

Although the cardinal feature of the pathogenesis of *Shigella flexneri* 2*a* infection involves the invasion of epithelial cells, because *Shigella flexneri* 2*a* can cause watery diarrhea, it has been hypothesized that *Shigella flexneri* 2*a* also produces an enterotoxin (Rout et al, *Gastroenterology*, 68:270–278 (1975); and Kinsey et al, *Infect. Immun.*, 14:368–371 (1976)). More specifically, the following observations have suggested the existence of enterotoxins in *Shigella flexneri* 2*a*:

1. Clinically in humans *Shigella flexneri* 2*a* infections are usually characterized by a period of watery diarrhea that precedes the onset of scanty dysenteric stools of blood and mucus (DuPont et al, *J. Infect. Dis.*, 119:296–299 (1969); and Stoll et al, *J. Infect. Dis.*, 146:177–183 (1982)). In mild cases, only watery diarrhea may occur, leading to a clinical picture undistinguishable from that due to enterotoxingenic *E. coli* infection (Taylor et al, *J. Infect. Dis.*, 153:1132–1138 (1986); and Taylor et al, *J. Clin. Microbiol.*, 26:1362–1366 (1988)).
2. When Shigella are fed to monkeys, three clinical syndromes are seen (Route et al, *Gastroenterology*, 68:270–278 (1975)). Some monkeys develop only dysentery; some exhibit only watery diarrhea and some exhibit watery diarrhea and dysentery. In vivo perfusion studies by Rout et al, *Gastroenterology*, 68:270–278 (1975)) showed that net transport of water into the lumen of the colon occurs in all ill animals. In contrast, only in the jejunum of monkeys with overt watery diarrhea (alone or followed by dysentery) does there occur net secretion of water, sodium and chloride ions; such net transport does not occur in the jejunum of monkeys manifesting dysentery without watery diarrhea. Net secretion in the jejunum was not accompanied by abnormal histological findings in this anatomic site of the small intestine.
3. The net secretion of water and electrolytes into the jejunum of monkeys with watery diarrhea requires the passage of Shigella through the jejunum (Kinsey et al, *Infect. Immun.*, 14:368–371 (1976)). This was demonstrated by bypassing the small intestine and inoculating Shigella directly into the cecum of monkeys. Of 16 monkeys who developed clinical illness, manifested dysentery, "... only rarely preceded by mild diarrhea". Net secretion of water and sodium into the colon was recorded in ill monkeys that developed dysentery following intracecal inoculation, while no abnormalities of water or electrolyte transport were observed in the jejunum of the ill animals.

Together, these observations suggest that Shigella elaborate an enterotoxin that elicits secretion early in the infection as the organisms pass through the jejunum.

However, except for the cytotoxin/neurotoxin/enterotoxin elaborated by *Shigella dysenteriae* (O'Brien et al, *Microbiol. Rev.*, 51:206–220 (1987); Keusch et al, *Pharmac. Ther.*, 15:403–438 (1982); and Fontaine et al, *Infect. Immun.*, 56:3099–3109 (1988)), but not by other Shigella species, little convincing proof has been generated to substantiate the contention that Shigella, other than *Shigella dysenteriae*, in fact produce enterotoxins.

More specifically, previous attempts in the art to detect enterotoxic activity in supernatants of *Shigella flexneri* 2*a* have yielded positive findings in only one instance. O'Brien et al, *Infect. Immun.*, 15:796–798 (1977), partially purified a toxin produced by *Shigella flexneri* 2*a* strain M4243 that was detectable in cell-free supernatants. This toxin stimulated fluid production in rabbit ileal loops, but was also cytotoxic for HeLa cells in monolayers and was lethal when inoculated intraperitoneally into mice. Further, it was not necessary to grow the bacteria in $Fe^{++}$-depleted medium in order to detect the enterotoxic activity. In addition, the cytotoxicity of the toxin described by O'Brien et al, supra, was neutralized by anti-sera to Shiga (*Shigella dysenteriae* 1) toxin.

Enterotoxic activity in cell-free supernatants of *Shigella flexneri* 2*a* and 3*a* was reported by Ketyi et al, *Acta Microbiol. Acad. Sci. Hung.*, 25:165–171 (1978); Ketyi et al, *Acta Microbiol. Acad. Sci. Hung.*, 25:219–227 (1978); and Ketyi et al, *Acta Microbiol. Acad. Sci. Hung.*, 25:319–325 (1978). Filtered ultrasonic lysates of two *Shigella flexneri* 2*a* and 3*a* strains were founds to give rapid fluid accumulation in rabbit ileal loops (4 hour assay). However, the loops showed no fluid accumulation when examined at 18–24 hours after inoculation. Only three loops were inoculated for each of the two test strains and when examined at 4 hours, only ⅔ for one strain and ⅓ for the other strain were positive. In addition, the Shigella were not cultured in $Fe^{++}$-depleted medium.

In the present invention, it was discovered for the first time that enterotoxic activity, which is clearly dissociated from cytotoxic activity, is expressed by *Shigella flexneri* 2*a* in the bacteria-free culture supernatant, and could be detected only after growth of the bacteria in $Fe^{++}$-depleted medium.

It has been reported that when grown in $Fe^{++}$-depleted medium, enteroinvasive *Escherichia coli* (EIEC) elaborate an enterotoxin (MW circa 68–80 kDa) that causes fluid accumulation in isolated rabbit ileal loops and an electrical response in Ussing chambers (Fasano et al, *Infect. Immun.*, 58:3717–3723 (1990)). Based on the similarities known to exist between enteroinvasive *E. coli* and Shigella (Levine et al, *J. Infect. Dis.*, 155:377–389 (1987)), it was postulated in the present invention that *Shigella flexneri* 2*a* would express an enterotoxin when grown in $Fe^{++}$-depleted medium.

In the present invention, it was unexpectedly disclosed that *Shigella flexneri* 2*a* produces two distinct enterotoxins, one encoded by the chromosome, and the other encoded by an invasiveness virulent plasmid. The latter enterotoxin was found in the present invention to be essentially the same as the EIEC enterotoxin.

SUMMARY OF THE INVENTION

An object of the present invention is to purify the two enterotoxins produced by *Shigella flexneri* 2*a.*

Another object of the present invention is to provide a method for culturing *Shigella flexneri* 2*a* so as to produce said enterotoxins.

A further object of the present invention is to provide antibodies having binding specificity for said enterotoxins.

An additional object is to identify, clone and sequence the genes encoding such enterotoxins.

Still another object of the present invention is provide *Shigella flexneri* 2*a* mutants which fail to produce at least one functional enterotoxin as a result of a mutation in a Shigella enterotoxin gene.

These and other objects of the present invention have been achieved in the detailed description of the invention provided below.

BRIEF DESCRIPTION OF THE DRAWINGS

FIGS. 6A–6D (SEQ ID NO:1) show the DNA sequence of EIET enterotoxin encoded by enteroinvasive *E. coli,* as well as the determined amino acid sequence.

FIGS. 7A–7D (SEQ ID NO:2) show the DNA sequence of ShET2 enterotoxin located on the *Shigella flexneri* 2*a* invasiveness plasmid, as well as the determined amino acid sequence.

FIGS. 9A–9B (SEQ ID NO:15) show the DNA sequence of ShET1 enterotoxin located on the *Shigella flexneri* 2*a* chromosome, as well as the determined amino acid sequence.

DETAILED DESCRIPTION OF THE INVENTION

Figure 1:
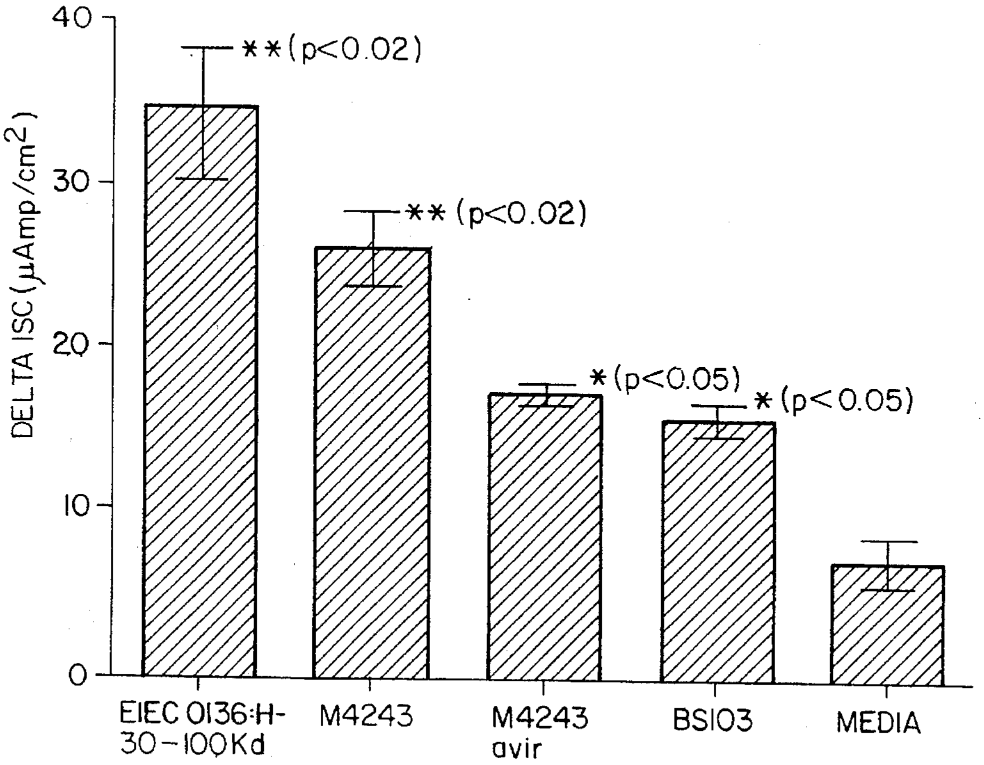
FIG. 1 shows the results of assays for enterotoxic activity in Ussing chambers when using culture supernatants of *Shigella flexneri* 2*a* strains M4243, M4243avir and BS103, the 30–100 kDa fraction of EIEC strain CVD/EI-34 (0136:H-) (as a positive control) and culture media (as a negative control). In these assays, variations in short-circuit current (delta $I_{sc}$) were measured.

In the present invention, the enterotoxins are obtained by culturing *Shigella flexneri* 2*a* in $Fe^{++}$-depleted medium and collecting the supernatant.

"$Fe^{++}$-depleted media" is an expression well-known and used in the art. This expression refers to iron-depleted media, such as syncase broth, treated, e.g., in CHELEX® (BioRad), a styrene divinyl benzene resin matrix with iminodiacetic acid exchange groups, to leave just traces of iron in the medium.

The particular culture medium employed is not critical to the present invention. Examples of such culture media include $Fe^{++}$-depleted syncase broth or L-broth plus ethylenediamine-N-N'-diacetic acid (EDDA). $Fe^{++}$-depleted syncase broth is the preferred culture medium since maximal production of the enterotoxin was obtained with this medium.

While the culture temperature and incubation period are not critical to the present invention, generally the culturing temperature will range from 30° to 37° C., preferably 36° to 37° C., and the incubation period will range from 24 to 72 hours, preferably 48 to 72 hours.

The enterotoxins can be purified from the supernatant by size exclusion and HPLC chromatography.

*Shigella flexneri* 2*a* is a well-known virulent Shigella serotype available from a variety of sources, such as the Center for Vaccine Development, the Center for Disease Control, the Walter Reed Army Institute of Research, the Uniformed Services University of the Health Sciences, and the Institut Pasteur. The particular strain of *Shigella flexneri* 2*a* employed in the present invention is not critical thereto. Examples of such *Shigella flexneri* 2*a* strains include M4243, M4243avir, *Shigella flexneri* 2*a* Chile 747, *Shigella flexneri* 2*a* Chile 3480 (Ferreccio et al, *Am. J. Epi.,* 134:614–627 (1991)); strain 2457T (Kotloff et al, *Infect. Immun.,* 60:2218–2224 (1992); and BS103 (Andrews et al, *Infect., Immun.,* 59:1997–2005 (1991)). The preferred *Shigella flexneri* 2*a* strains employed in the present invention are *Shigella flexneri* 2*a* strain M4243 and M4243avir.

*Shigella flexneri* 2*a* strain M4243 and its plasmid-cured derivative M4243avir can be obtained from, e.g., Dr. Samuel B. Formal of the Walter Reed Army Institute of Research, Washington, D.C. BS103 can be obtained from Dr. Anthony Maurelli of the Uniformed Services University of the Health Sciences, Bethesda, Md.

The antibodies having binding specificity to the two enterotoxins of the present invention may be polyclonal or monoclonal. Polyclonal antibodies to the purified enterotoxins can be prepared by conventional means as described in *Antibodies: A Laboratory Manual,* Harlow and David Lane, Eds., Cold Spring Harbor Laboratory Press (1988). Monoclonal antibodies to the purified enterotoxins can be prepared by conventional means as described in Kohler et al, *Nature,* 256:495–497 (1975).

Monoclonal antibodies obtained using purified enterotoxins may be used to induce a passive immunity against Shigella enteric infection. Such antibodies will bind *Shigella flexneri 2a* enterotoxins, thus preventing these interaction with the cellular receptor, and preventing the stimulation of water and electrolyte secretion. The total amount of antibodies used to induce passive immunity is generally about 10 mg to 10 g. The total amount of toxoid used to produce such antibodies is generally about 500 μg to 5.0 mg.

The substantially pure enterotoxins of the present invention are also useful for the development of a non-reactogenic *Shigella flexneri* 2*a* candidate live oral vaccine. As background, in the United States, *Shigella flexneri* 2*a* is one of the most common serotype of Shigella associated with disease. In developing countries of the world, *Shigella flexneri* is the most common serogroup of Shigella causing diarrheal disease and *Shigella flexneri* 2*a* is often the single most common serotype. Prospective epidemiologic studies in a low socioeconomic community in Santiago, Chile, where Shigella infections are endemic, have shown that an initial clinical episode of shigellosis confers significant protection against subsequent disease due to the same serotype (Ferroccio et al, *Am. J. Epidemiol.,* 134:614–627 (1991)). The immunizing effect of diarrheal illness due to wild-type Shigella has also been demonstrated in a volunteer model of experimental shigellosis where an initial clinical infection due to *Shigella flexneri* 2*a* (DuPont et al, *J. Infect. Dis.,* 125:12–16 (1972)) or Shigella sonnel (Herrington et al, *Vaccine,* 8:353–357 (1990)) conferred significant protection against re-challenge with the homologous wild-type organism. Together these observations suggest that it may be possible to protect against shigellosis with a vaccine that requires only a single dose.

There have been many attempts to develop attenuated strains of Shigella to serve as vaccines. Some attempts have met with limited success. In the 1960s, streptomycin-dependent strains of *Shigella flexneri* 2*a* and other serotypes were developed and utilized as live oral vaccines (Mel et al, *Bull. WHO,* 32:647–655 (1965); Mel et al, *Bull. WHO,* 39:375–380 (1968); and Mel et al, *Acta Microbiol. Acad. Scient. Hung.,* 21:109–114 (1974)). These streptomycin-dependent strains were safe and conferred significant serotype-specific protection against shigellosis in most of the controlled field trials of efficacy that were carried out (Mel et al, *Bull. WHO,* 32:647–655 (1965); Mel et al, *Bull. WHO,* 39:375–380 (1968); Mel et al, *Acta Microbiol. Acad. Scient. Hung.,* 21:109–114 (1974); and Levine et al, *Am. J. Epidemiol.,* 133:424–429 (1976)). However, the streptomycin-dependent Shigella vaccinees suffer from certain drawbacks. One is the fact that multiple spaced doses have to be given to confer protection (four doses over a two-week period containing large numbers ($2–4×10^{10}$) of viable vaccine organisms). Moreover, protection is relatively short-lived. A booster dose has to be given after one year in order to maintain protection (Mel et al, *Acta Microbiol. Acad. Scient. Hung.,* 21:109–114 (1974)). Colonial mutant *Shigella flexneri* 2*a* vaccine strain $T_{32}$ described in Istrari et al, *Arch. Roumaines Pathol. Exp. Microbiol.,* 24:677–686 (1985), is also well-tolerated and protective (Wang Bing Rui, *Arch. Roumaines Pathol. Exp. Microbiol.,* 43:285–289 (1984)), but still requires multiple doses.

Because of the above-mentioned drawbacks of the streptomycin-dependent and $T_{32}$ vaccines of the 1960s, various investigators have attempted to make more immunogenic Shigella vaccines that can protect following the administration of just a single dose. The approaches taken have included:

(1) introducing specific segments of the chromosome of *E. coli* K-12 into Shigella by conjugation (Formal et al, *Dev. Biol. Stand.,* 15:73–78 (1971); and Levine et al, *J. Infect. Dis.,* 127:261–270 (1973));

(2) introducing DNA encoding protective Shigella antigens into *E. coli* K-12 (Formal et al, Infect. Immun., 46:465–469 (1984)); and (3) inactivating genes of the aromatic amino acid biosynthesis pathway, thereby rendering the Shigella nutritionally dependent on substrates that are not available in human tissues (Lindberg et al, *Vaccine,* 6:146–150 (1988); and Karnell et al, *Rev. Infect. Dis.,* 13(4):S357–361 (1991)).

Regrettably, each of the above approaches has met with limitations. That is, hybrids in which Shigella carrying attenuating *E. coli* DNA are unstable and can revert to full virulence (Levine et al, *J. Infect. Dis.,* 127:261–270 (1973)). Further, the most recent generation of *E. coli* expressing Shigella antigens has been associated with side reactions in vaccinees, including fever, mild diarrhea and every dysentery in some individuals (Kotloff et al, *Infect. Immun.,* 60:2218–2224 (1992)). Finally, some recipients of ΔaroD *Shigella flexneri* developed mild diarrhea (Karnell et al, *Rev. Infect Dis.,* 13(4):S357–361 (1991)). It has been hypothesized in the present application that the residual diarrhea encountered in these various *Shigella flexneri* candidate vaccine strains is likely due to the two enterotoxins.

Accordingly, *Shigella flexneri* 2*a* vaccine candidates can be constructed which, e.g., in addition to containing other attenuating mutations, express one or two toxoids, rather than the enterotoxins. This can be accomplished by deleting the portion of the enterotoxin genes that encodes the biologically active "toxic" site, leaving intact immunogenic sequences of the protein. Specifically, a *Shigella flexneri* 2a strain in which deletion mutations are introduced in at least one aro gene (aroA, aroC, or aroD) of the Shigella chromosome, rendering the strain auxotrophic for paraaminobenzoic acid, a substrate that cannot be sufficiently scavenged in vivo in humans, can be constructed, such as strain CVD1203 (ATCC No. 55556) prepared in Example 8 below.

In addition, the strain will preferably have an independently attenuating, deletion mutation in the virG gene, which is found on the 140 MD invasiveness plasmid of *Shigella flexneri 2a.* This plasmid gene, also known as icsa (Sansonetti et al, Vaccine, 7:443–450 (1989)), is involved with the intracellular and intercellular spread of Shigella. This mutation is also present in CVD1203.

Recognizing that the vaccine candidate, e.g., CVD1203, may still not be sufficiently attenuated with just these mutations (since the ability to produce enterotoxins remains intact), the enterotoxin genes can be mutated. One type of mutation, e.g., a deletion of substantially all of the enterotoxin genes, will totally inactivate enterotoxin production, resulting in a non-enterotoxinogenic strain. A second mutation, e.g., a deletion of part of the enterotoxin genes, will result in expression of toxoids, i.e., modified proteins that lacks the toxicity of the toxins but retains immunogenic moieties. This alternative mutation will result in a vaccine candidate strain that expresses two toxoids. These toxoids can be used to induce active immunity against *Shigella flexneri* infection.

The particular size of the deletion is not critical to the present invention, and can be readily determined based upon whether one desires to totally inactivate the enterotoxins, or simply produce toxoids. As shown in Example 7, ShET1 is encoded by two distinct genes (FIGS. 9A and 9B, Seq. ID NO:15). Based on similarities between ShET1 genes and genes encoding for other endotoxins, such as cholera toxin or heat-labile enterotoxin of enterotoxigenic *E. coli,* the large orf encodes for the active subunit. Thus, an internal deletion of this orf should give rise to the production of an immunogenic toxoid.

The isolated DNA molecules of the present invention encoding the enterotoxin genes can be cloned in any suitable plasmid or vector, and used, e.g., to produce large amounts of DNA for use as probes or to integrate mutated enterotoxin genes into vaccine strains.

The expression "isolated" is used herein to mean set apart from its natural environment, e.g., the DNA molecules are separated from the parent chromosome or parent plasmid from which they were originally obtained in the present invention. Thus, "isolated" as used herein includes the presence of the DNA molecules in a foreign host or foreign plasmid.

The following examples are provided for illustrative purposes only and are in no way intended to limit the scope of the present invention.

EXAMPLE 1

Production of Enterotoxins

A. Preparation of Culture Filtrate Fraction

*Shigella flexneri 2a* strain M4243 and its plasmid-cured derivatives M4243avir and BS103, were grown overnight at 37° C. with shaking (200 rpm) in 5.0 ml of CHELEX® (BioRad, Richmond, Calif.) treated, $Fe^{++}$-depleted syncase broth (O'Brien et al, *J. Infect. Dis.,* 136:763–759 (1982)). CHELEX® binds to the iron present in the broth. All culture vessels employed were either new plastic or borosilicate glass soaked overnight in 6.0N HCl, and rinsed in distilled deionized water to ensure the absence of iron. 50 µl of the resulting culture broth were then subcultured in 5.0 ml of $Fe^{++}$-depleted syncase broth in baffled Fernbach flasks, and incubated for an additional 48 hours under the above conditions. After 72 hours of incubation, the cultures were harvested by centrifugation of 12,000×g for 20 minutes at 4° C. and the supernatants were passed through a 0.45 µm filter membrane (Millipore Products, Bedford, Mass.) to obtain a "sterile supernatant".

B. Rabbit Ileal Loop Test

Whole cultures of *Shigella flexneri 2a* strain M4243 and its plasmid-cured derivative M4243avir, along with their respective sterile supernatants, obtained as described above, were tested in a standard rabbit ileal loop test. Supernatants of EIEC strain CVD/EI-34 (0136:H-) (which induces fluid accumulation in rabbit ileal loops) and non-pathogenic *E. coli* HS, were also included in each experiment as positive and negative controls, respectively (Fasano et al, *Infect. Immun.,* 58:3717–3723 (1991)). EIEC strain CVD/EI-34 (0136:H-) was obtained from the Center for Vaccine Development strain collection. *E. coli* HS was obtained from Dr. Herman Schneider, Walter Reed Army Institute of Research.

More specifically, male adult New Zealand white rabbits weighing 2–3 kg were starved for 24 hours but allowed water ad libitum. These animals were then anesthetized by intramuscular administration of a cocktail of 50 mg/kg ketamine and 1.0 mg/kg acepromazine, followed by intramuscular administration of 7.0 mg/kg xylazine.

Bacterial cultures were grown to reach $10^8$–$10^9$ CFU/ml. Whole cultures, or the respective sterile supernatants, in a standard volume of 1.0 ml, were injected into the lumen of the intestine of the anesthetized rabbits near a tie closest to the mesoappendix (Moon et al, *Ann. NY. Acad. Sci.,* 176:197–211 (1971)); a second tie was made to isolate the site of inoculation. Proceeding proximally along the ileum, a series of five to six loops 7–8 cm long separated by double ties were isolated and inoculated (Moon et al, *Ann. NY. Acad. Sci.,* 176:197–211 (1971)). After 18 hours of incubation, the animals were sacrificed, the fluid volume and length of the loops were measured, and sections of intestine from each loop were fixed in 10% (v/v) formalinized saline and examined by light microscopy. The results of the loop test are shown in Experiment 1 in Table 1 below.

TABLE 1

| Fluid Accumulation (ml/cm) in Rabbit Ileal Loops | |
|---|---|
| Experiment 1 | |
| M4243 bacteria (5) | 1.06 ± 0.34* |
| M4243 supernatant (5) | 0.52 ± 0.10** |
| M4243avir bacteria (5) | 0.21 ± 0.50 |
| M4243avir supernatant (5) | 0.24 ± 0.09 |
| HS supernatant (5) | 0.09 ± 0.06 |
| Experiment 2 | |
| M4243 supernatants: | |
| L broth, 24 hours (4) | 0.01 ± 0.01 |
| L broth, 72 hours (4) | 0.04 ± 0.03 |
| Minimal $Fe^{++}$ broth, 24 hours (4) | 0.43 ± 0.11* |
| Minimal $Fe^{++}$ broth, 72 hours (4) | 0.47 ± 0.14* |
| HS supernatant: | |
| Minimal $Fe^{++}$ broth, 24 hours (4) | 0.01 ± 0.01 |

In the Table above, the results are expressed as mean ± SE for (n) animals. The bacterial cultures were grown for 72 hours unless otherwise indicated. *$p < 0.01$ compared to HS; ** $p < 0.05$ compared to HS.

As shown in Experiment 1 in Table 1 above, the intestinal loops injected with the positive control, i.e., whole viable cultures of M4243, and sterile culture supernatant therefrom, showed pronounced fluid accumulation at 18 hours post-inoculation, with the whole viable culture showing a two-fold greater fluid accumulation. Further, as shown in Experiment 1 in Table 1 above, fluid accumulation induced by M4243avir (both whole culture and sterile supernatant) was not significantly higher than the negative control strain HS.

The fluid to gut length recorded in the rabbit ileal loops, 0.5 ml/cm, measured using graduated syringes (fluid) and a scale (length), was substantially less than seen with enterohemorrhagic *E. coli* (EHEC) strain 933J, serotype (0157:H7), where ratios of 1.5–2.0 ml/cm occur. However, the recorded fluid to gut length measured using graduates syringes (fluid) and a scale (length) still represents definite evidence of net secretion and fluid accumulation.

On histologic examination of the sections of intestine from each loop, severe tissue damage was observed with whole cultures of M4243, characterized by prominent necrosis of the luminal epithelium and marked villus atrophy. In contrast, with M4243 sterile culture supernatant, no tissue damage was detected. Further, no tissue damage was observed with whole cultures of M4243avir or sterile supernatants therefrom. Moreover, no tissue damage was observed with tissue incubated with the negative control strain HS.

To determine whether the time of incubation and the iron content in the medium are crucial for the full expression of this enterotoxic moiety, *Shigella flexneri 2a* strain M4243 was cultured in $Fe^{++}$-containing medium (L-broth) and $Fe^{++}$-depleted medium (syncase broth). After 24 and 72 hours of incubation for each medium, sterile, supernatants were obtained and then rejected in ileal loops, as described above. The results are shown in Experiment 2 in Table 1 above.

As shown in Experiment 2 in Table 1 above, $Fe^{++}$-depleted culture conditions are required in order to detect expression of the enterotoxin. Further, enterotoxin expression was not notably affected by the length of incubation.

The results obtained in the rabbit ileal loop assay were compatible with elaboration of an enterotoxin by M4243.

C. Ussing Chambers

These experiments were performed as previously described by Guandalini et al, *J. Pediatr. Gastroenterol. Nutr.,* 6:953–960 (1987). Briefly, male adult New Zealand white rabbits weighing 2–3 kg were anesthetized by methoxyflurane inhalation and then sacrificed by air embolism. A 20 cm segment of distal ileum was removed, opened along the mesenteric border, rinsed free of intestinal contents, and stripped of muscular and serosal layers. Four pieces of intestine so prepared were then mounted in lucite Ussing chambers (1.12 $cm^2$ opening) and bathed in Ringer's solution containing 53 mM NaCl, 5.0 mM KCl, 30.5 mM $Na_2SO_4$, 30.5 mM mannitol, 1.69 mM $Na_2HPO_4$, 0.3 mM $NaH_2PO_4$, 1.25 mM $CaCl_2$, 1.1 mM $MgCl_2$ and 25 mM $NaHCO_3$. During the experiment, the tissue was kept at 37° C. and gassed with 95% $0_2$–5% $CO_2$. Once the tissue reached a steady-state condition, 300 μl of either M4243, M4243avir or BS103 sterile supernatants from $Fe^{++}$-depleted cultures were added to the mucosal surface, resulting in a 1:33 dilution of the original culture filtrate concentration (0.3 ml into 10 ml of Ringer's solution). 300 μl of either M4243, M4243avir or BS103 sterile supernatants were also added to the serosal side to preserve osmotic balance. Variation in transepithelial electrical potential difference (delta PD), total tissue conductance (Gt) and short-circuit current (delta $I_{sc}$) were recorded. The 30–100 kDa supernatant fraction from EIEC (0136:H-) and CHELEX®-treated syncase broth (culture media) were also tested in the same manner as positive and negative controls, respectively. Four animals were employed for each test. The results are shown in FIG. 1.

As shown in FIG. 1, the overall increase in $I_{sc}$ was significantly greater for the M4243 supernatant as compared to the negative control (culture medium) (**=p<0.02), and similar in magnitude to that induced by the positive control (EIEC 0136:H-). On the other hand, supernatant from the plasmid-cured derivatives M4243avir and BS103 expressed significantly less enterotoxin in comparison with the plasmid-containing parent strain (*=p<0.05). However, the enterotoxic activity of the M4243avir and BS103 supernatants was nevertheless significantly greater than the negative control (culture medium) (*=p<0.05). Possible interpretations of such results include: (1) a plasmid-encoded regulation factor that regulates a chromosomal toxin gene; (2) multiple copies of the same gene located both on the *S. flexneri 2a* chromosome and the plasmid; or (3) a gene on the invasiveness plasmid encoding for a distinct enterotoxic factor. As discussed in detail below, this last hypothesis turned to be correct.

The plasmid-cured derivative of strain M4243 showed less enterotoxic activity compared to the wild-type in both ileal loops and in Ussing chambers. Only in Ussing chambers did M4243avir induce changes that were significantly different from the negative control; this could be due to the higher sensitivity of the Ussing chamber technique as compared to the ileal loop assay. These data suggest that, while not absolutely necessary for the effect, the virulence plasmid of *Shigella flexneri 2a* M4243 enhances enterotoxic activity.

D. Enterotoxin Neutralization

EIEC (0136:H-) and *Shigella flexneri 2a* share many similarities, e.g., surface antigens, identical plasmids (pInv), clinical manifestations, etc. Thus, neutralization experiments were carried out to determine if there is any immunological relatedness between the enterotoxin produced by EIET (0136:H-) and the enterotoxin produced by M4243.

More specifically, 600 μl of the 30–100 kDa fraction of M4243 sterile supernatant (see Section E. below) were incubated for 60 min at 37° C. with 60 μl of anti-ShET polyclonal sera (anti-*Shigella flexneri* 2a enterotoxin) or with anti-EIET polyclonal sera (anti-enteroinvasive *E. coli* enterotoxin) or with pre- or post-challenged convalescent sera.

Anti-ShET polyclonal sera, anti-EIET polyclonal sera, and convalescent sera were obtained as described in Example 2.

The resulting samples were tested in Ussing chambers as described in Section C. above with half of each mixture added to each side of a chamber. The results are shown in FIGS. 2A–2D.

As shown in FIGS. 2A–2D, the electrical response in Ussing chambers was drastically reduced when M4243 supernatant was pre-incubated with polyclonal rabbit antibodies raised against the *Shigella flexneri 2a* enterotoxins (anti-ShETs) or with convalescent sera from volunteers who had been challenged with *Shigella flexneri 2a.* This neutralization was not observed in either of the pre-immune sera control experiments in which responses were similar to those seen when testing the active fraction alone.

Only a partial cross-neutralization was observed when the M4243 supernatant was pre-incubated with polyclonal antibodies raised against the enteroinvasive *E. coli* enterotoxin (anti-EIET).

In FIGS. 2A–2D, the number of animals tested was 4. Values are mean ±SE. *=p<0.05 and * *=p<0.02 compared to PBS (the negative control).

Taken together, these results suggest that *S. flexneri* supernatant probably contains two enterotoxin moieties, ShET1 (whose gene is located on *S. flexneri* chromosome) and ShET2 (whose gene is located on the invasiveness plasmid). Both enterotoxins were neutralized when anti-*S. flexneri* 2a antiserum was used. The ability of EIEC antiserum to partially neutralize the *S. flexneri 2a* supernatant enterotoxicity was due to the high similarity (99%) of EIET gene with ShET2 gene (see below).

E. Estimate of Molecular Mass

To obtain an estimate of the $M_r$ of the *Shigella flexneri 2a* enterotoxins, sterile supernatant of M4243 was fractionated by ultracentrifugation through DIAFLO ultrafiltration membranes (Amicon Corp., Danvers, Mass.). YM100 (100,000-MW cutoff) and YM30 (30,000-MW cutoff) membranes were utilized to produce fractions defined by these size limits. Membrane retentates were washed free of lower molecular weight species with phosphate buffered saline (pH 7.3) (PBS), by two successive 10:1 volume dilutions with PBS, reconcentration, and final reconstitution to the original volume in PBS.

The individual fractions, representing coarse molecular weight pools of >100 kDa, 30–100 kDa and 0.5–30 kDa, were tested for enterotoxic activity in Ussing chambers and ileal loops. The results are shown in FIG. 3A–3B.

Figure 3A:
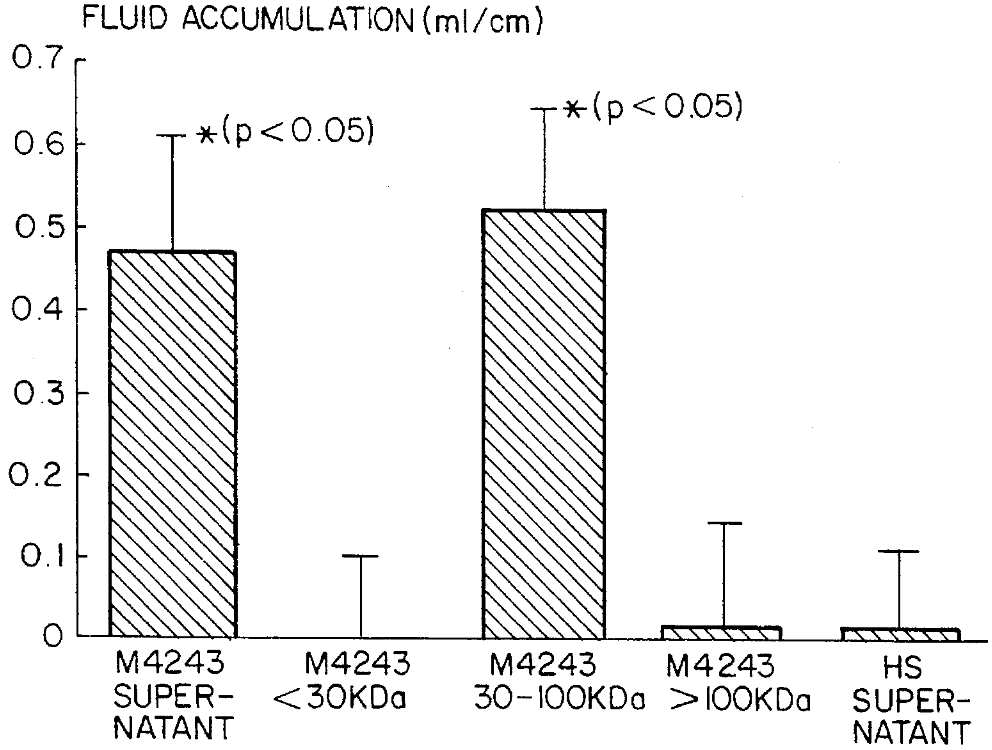
FIGS. 3A–3B shows the molecular mass determination of the *Shigella flexneri* 2*a* strain M4243 enterotoxic moieties when assayed in rabbit ileal loops (FIG. 3A) and in Ussing chambers (FIG. 3B). In the rabbit ileal loop assays, fluid accumulations were measured and in the Ussing chambers, variations in short-circuit current (delta $I_{sc}$) were measured.
Figure 3B:
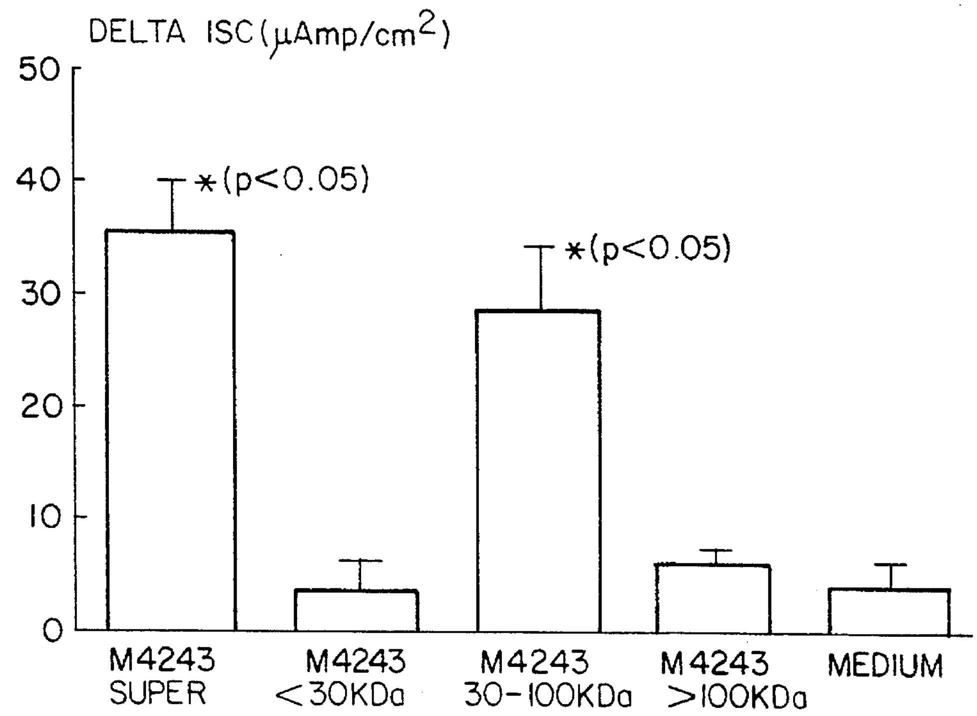

As shown in FIGS. 3A–3B, both ileal loop (FIG. 3A) and Ussing chamber (FIG. 3B) assays localized the active enterotoxic fraction within the 30–100 kDa size range.

In FIGS. 3A–3B, the number of animals tested was 4. Values are means ±SE. *=p<0.05 and **=p<0.02 compared to the other fractions and the negative control.

F. Cytotoxicity Assay

To establish whether there is a correlation between enterotoxic activity and cytotoxic activity, the following experiments were carried out.

A cell lysate was obtained as follows: Cultures from strain M4243 were harvested by centrifugation at 12,000×g for 20 minutes at 4° C. Supernatants were passed through a 0.45 μm filter, and retained for assay. The bacterial cells were then washed twice in PBS, resuspended in 1.5 ml of PBS and disrupted in a French pressure cell at 12,000 lb/in$^2$ to obtain a cell lysate (Fasano et al, *Infect. Immun.*, 58:3717–3723 (1991)). The cell lysate was then mixed with 3.5 ml of PBS (final volume 5.0 ml), clarified by centrifugation at 18,000×g for 20 minutes at 4° C., and filter-sterilized using a 0.45 μm membrane.

Fractions of the culture supernatant of strain M4243 were obtained as described in Section E. above.

Cytotoxicity assays were performed on the cell lysate and 3 different culture supernatant fractions (less than 30 kDa, 30–100 kDa, and more than 100 kDa), 10 with Vero cells by the method of Gentry et al, *J. Clin. Microbiol.*, 12:361–366 (1980)). Serial two-fold dilutions (1:2 to 1:64) of the culture supernatant fractions and cell lysate were tested, and the cytotoxic dose required to kill 50% of the Vero cells (CD50) was estimated spectrophotometrically (Gentry et al, *J. Clin. Microbiol.*, 12:361–366 (1980)).

Whole culture supernatants and cell lysates of enterohemorrhagic *E. coli* (EHEC) strain 933J, serotype 0157:H7, which elaborates Shiga-like toxin 1 (SLT1), were used as the positive control in the Vero cell cytotoxicity assay (Fasano et al, *Infect. Immun.*, 58:3717–3723 (1991)). The whole supernatant of non-pathogenic *E. coli* strains HS, which has been used extensively as a negative control in assays of pathogenicity and in clinical studies (Levine et al, Lancet, I:1119–1122 (1978); and Levine et al, *J. Infect. Dis.*, 148:699–709 (1983)), was used as a negative control in the Vero cell cytotoxicity assay.

Since the positive control (EHEC) killed more than 50% of the Vero cells at a 1:64 dilution, a 10-fold dilution of both supernatants and lysates from EHEC was tested. Cytotoxic titers were expressed as the reciprocal of the $CD_{50}$/mg protein of the 30–100 kDa culture supernatant fraction or cell lysate; the protein content was measured by the method of Bradford, *Anal. Biochem.*, 72:248–254 (1976)).

Both supernatant and lysate of the positive control strain EHEC strain 933J serotype (0157:H7) showed a high level of cytotoxicity ($0.5\times10^3$ and $3.4\times10^4$ $CD_{50}$/mg protein, respectively). In contrast, the supernatant of HS, the negative control, showed no cytotoxic activity. Against these two extremes, M4243 exhibited a low-level of cytotoxic activity which was restricted to the less than 30 kDa supernatant fraction ($4.2\times10^2$ $CD_{50}$/mg protein) and the cell lysate ($5.1\times10^2$ $CD_{50}$/mg protein).

The cytotoxic assay described above was repeated, except that HeLa cells were substituted for Vero cells. As a result of this experiment, it was determined that the 30–100 kDa fraction obtained from *Shigella flexneri 2a* supernatant and cell lysate also does not possess any cytotoxic activity against HeLa cells. On the other hand, as expected, and consistent with the results obtained using Vero cells, only the less than 30 kDa supernatant fraction obtained from *Shigella flexneri 2a* possesses cytotoxic activity against HeLa cells ($3.2\times10^2$ $CD_{50}$/mg protein). Also as expected, the cell lysate fraction from *Shigella flexneri 2a,* which contains the less than 30 kDa fraction possesses cytotoxic activity against HeLa cells ($4.4\times10^2$ $CD_{50}$/mg protein).

Thus, the enterotoxin (30–100 kDa fraction) activity and cytotoxin (less than 30 kDa fraction) activity found in *Shigella flexneri* 2*a* are the result of two distinct moieties.

Hence, the enterotoxin appears to be responsible for the diarrhea induced by *Shigella flexneri* 2a, since the 30–100 kDa fraction (where the enterotoxic activity was localized) was responsible for fluid accumulation in rabbit ileal loops and in electrical responses in Ussing chambers.

EXAMPLE 2

Preparation of Antisera

A. Preparation of Antibodies in Rabbits 1.0 ml of the 30–100 kDa fraction from the supernatant of *Shigella flexneri* 2*a* strain M4243 that showed enterotoxic activity was mixed with an equal volume of Freund's complete adjuvant and inoculated intramuscularly in four separate sites in male New Zealand white rabbits. A booster dose (1.0 ml) was administered four weeks later, and one month thereafter the animals were bled to obtain antisera. Antisera to EIEC enterotoxin (EIET) from strain CVD/EI-34 (0136:H-) was prepared in the identical manner. These antisera are herein referred to as anti-*Shigella flexneri 2a* enterotoxins (anti-ShETs) and anti-enteroinvasive *E. coli* enterotoxin (anti-EIET).

B. Preparation of Antibodies in Humans

Figure 4:
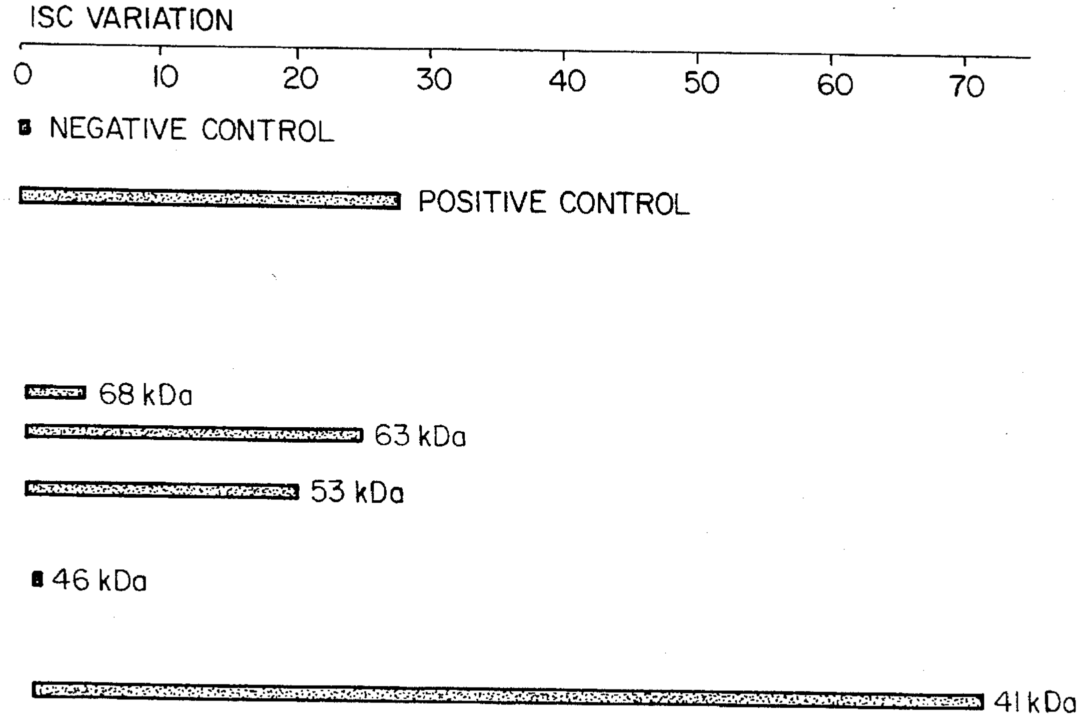
FIG. 4 shows the results of assays for enterotoxic activity in Ussing chambers when using protein bands from SDS-PAGE obtained from strain M4243avir (containing only ShET1 enterotoxin) that represent the 65–75 kDa column fraction, an extract of an unused strip of nitrocellulose (negative control), and a sample representing the 65–75 kDa column fraction (positive control). Values are given as variation (μAmp/$cm^2$) with N representing the number of observations on independently prepared samples.
Figure 2A:
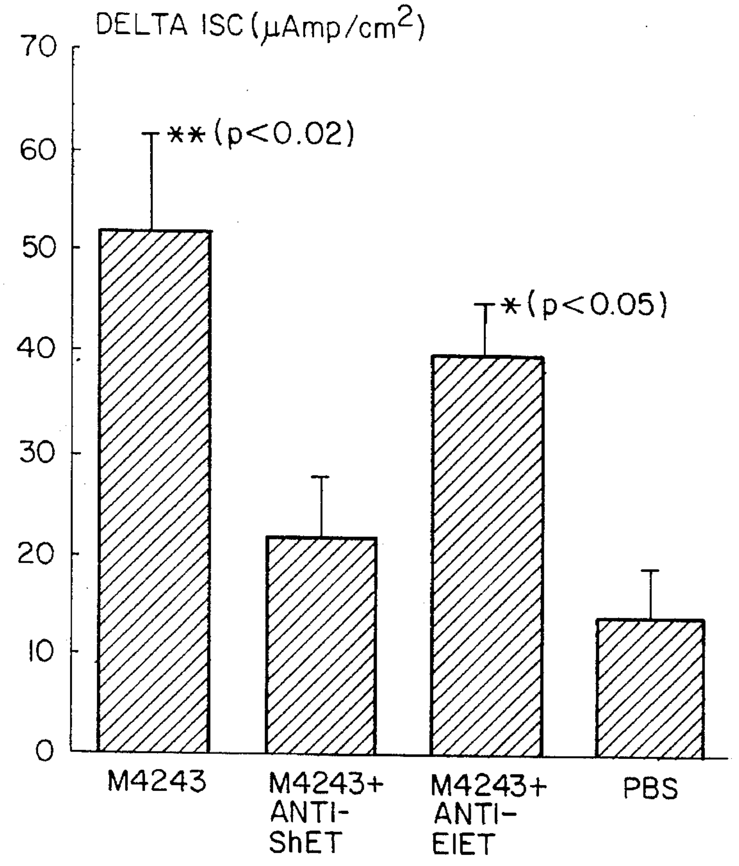
FIGS. 2A–2D show the results of assays for enterotoxic activity in Ussing chambers when using *Shigella flexneri* 2*a* strain M4243 culture supernatant which was first neutralized with anti-sera against the *Shigella flexneri* 2*a* enterotoxins (anti-shETs), with anti-sera against the EIEC enterotoxin (anti-EIET), with pre-challenge sera or post-challenge sera of volunteers challenged with wild-type *Shigella flexneri* 2*a.* In these assays, variations in short-circuit current (delta $I_{sc}$) (FIG. 2A and 2C and transepithelial electrical potential differences (delta PD) (FIG. 2B and 2D) were measured.
Figure 2B:
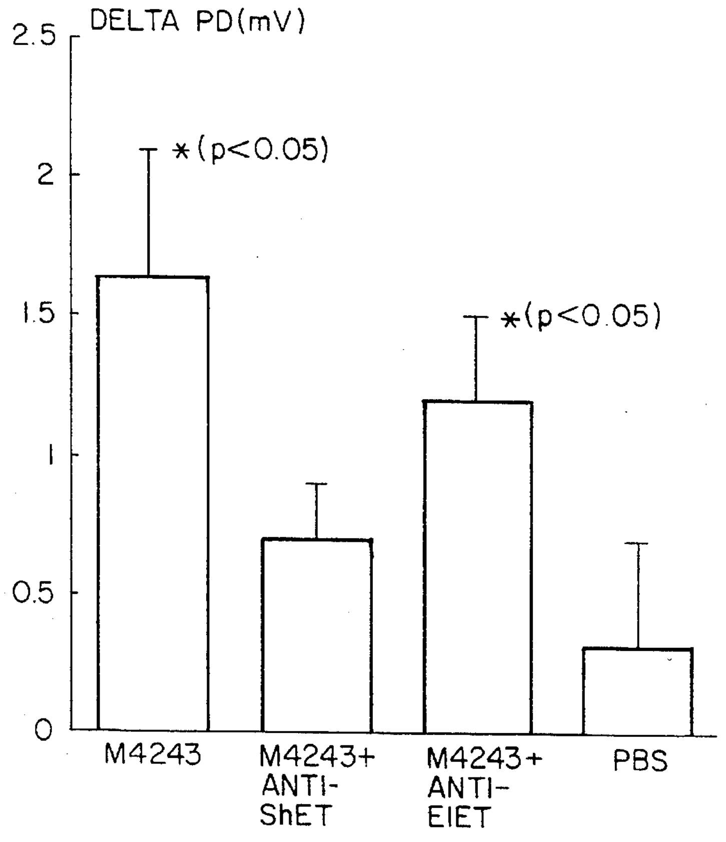
Figure 2C:
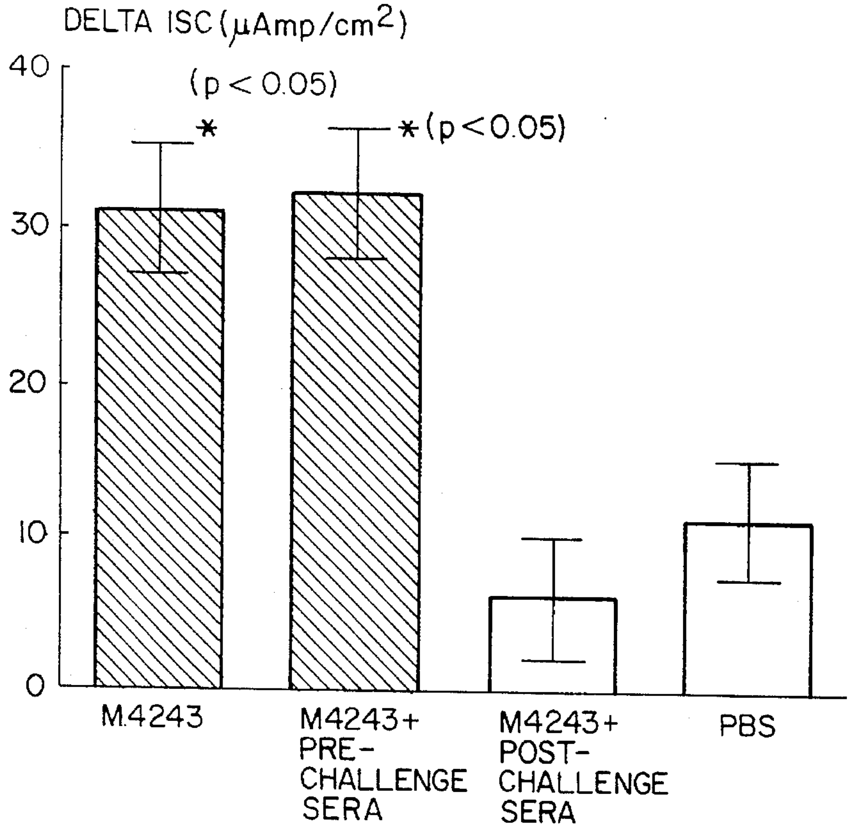
Figure 2D:
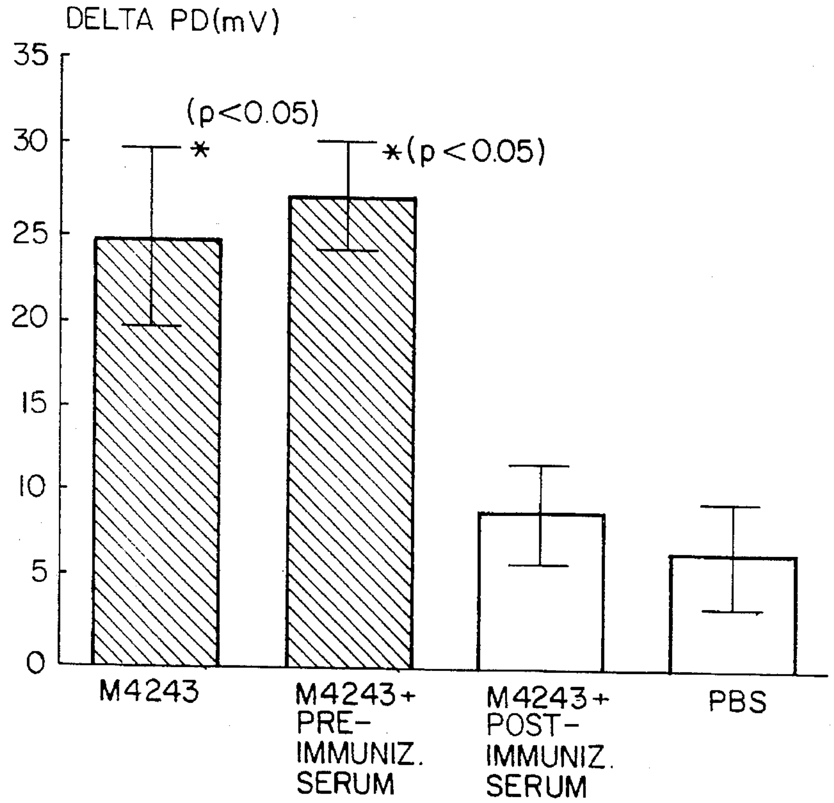

Pre- and post-challenged (convalescent) serum pools from 10 adult volunteers who developed diarrhea after ingesting *Shigella flexneri 2a* M4243 (Kotloff et al, *Infect. Immun.*, 60:2218–2224 (1992)) were prepared for use in neutralization experiments in Ussing chambers (FIGS. 2C and 2D), and for Western immunoblots (FIG. 4).

EXAMPLE 3

Purification and Partial Sequencing of Shigella Enterotoxin 1 (ShET1)

A. Purification

Large-scale preparation of *Shigella flexneri* 2*a* enterotoxin was undertaken in order to obtain sufficient material for further characterization and analyses. Plasmid-cured *S. flexneri 2a* M4243avir was used in order to avoid expression of both ShET2 and plasmid-encoded membrane associated proteins (Hale et al, *Infect. Immun.*, 50:620–629 1985)) which are known to be similar in size to the fractions exhibiting enterotoxic activity and to be antigenic in volunteers (Van De Verg et al, *J. Infect. Dis.*, 166:158–161 (1992)).

More specifically, plasmid-cured *Shigella flexneri 2a* was inoculated into 30 liters of L-broth containing 25 μg/ml of the iron-chelator, ethylenediamine-di-o-hydroxyphenylacetic acid (EDDA) (Rogers, *Infect. Immun.*, *Z*:445–456 (1973)), and incubated overnight at 37° C. in the New Brunswick Scientific 30 liter fermentor. Bacterial cells were removed by centrifugation at 5,000×g in a Sharples industrial centrifuge, and the supernatant was filtered through a 0.45 μm filter. This filtrate (approximately 30 liters) was fractionated to isolate and concentrate 100-fold the moieties falling within the 30–100 kDa range as described above, except Pellicon tangential flow cassettes (Millipore) were used for ultrafiltration processing of these larger volumes. This filtrate exhibited enterotoxic activity similar to levels observed for smaller batches employing the plasmid-cured strain.

A 10 ml aliquot of the 30–100 kDa concentrate was then further fractionated by replicate separations with an HPLC size exclusion column (SEC-2000, 7.5×600 cm with guard column, Phenomenex, Torrance, Calif.). Fractions were eluted from the column with PBS at 0.5 ml/min. The fractions containing moieties in the 65–75 kDa range were collected, pooled and concentrated by vacuum dialysis to 1.0 ml employing a 10 kDa membrane (MicroProDiCon, Spectrum Medical Industries, Los Angeles, Calif.). An aliquot of this material was reserved for enterotoxin assay, and the remainder was separated by sodium dodecyl sulfate polyacrylamide gel electrophoresis (SDS-PAGE) (Laemmli, *Nature,* 227:680–685 (1970)) using an 11 cm preparative well with peripheral marker lanes. The resultant 18 bands were transferred to a nitrocellulose membrane by the method of Towbin et al, (Towbin et al, *Proc. Natl. Acad. Sci. U.S.A.,* 76:4350–4354 (1979)).

Multiple 2 mm wide vertical strips of the nitrocellulose membrane were prepared and stained with colloidal gold (Aurodye, Janssen Pharmaceutica, Piscataway, N.J.) to visualize protein bands, or reacted with the pooled convalescent sera by Western immunoblotting techniques (Vial et al, *J. Infect. Dis.,* 158:70–79 (1988)).

Five protein bands were identified by the convalescent serum Western strips indicating their antigenic relatedness. The five protein bands were aligned with the remainder of the nitrocellulose blot which had been reversibly stained with Ponceau S (colloidal gold (Harlow et al, *Antibodies: A Laboratory Manual,* p. 494 (1988)). Using a scalpel, bands of about 10 cm in length corresponding to immunoreactive material from each of the five protein bands were carefully excised by identification and alignment with the Western and protein stained strips. Material from each of these bands were eluted (Montelero, *Electrophoresis,* 8:432–438 (1987)) by dissolution of the nitrocellulose in 200 μl of dimethyl sulfoxide, addition of four volumes of water to precipitate the nitrocellulose, followed by centrifugation at 10,000×g, and dialysis of the supernatant against PBS.

Each sample, in addition to the reserved 65–75 kDa sizing column fraction, and material from a mock-blotted and extracted nitrocellulose strip as positive and negative controls, respectively, was then tested for enterotoxic activity in Ussing chambers, as discussed in Example 1 above. The results are shown in FIG. 4.

As shown in FIG. 4, three of the bands, of approximate MW 63 kDa, 53 kDa and 41 kDa, exhibited enterotoxic activity. Replicates of a band corresponding to a MW of 41 kDa showed a consistent mean rise in $I_{sc}$ of 70.4 $\mu Amp/cm^2$, whereas the 63 kDa and 53 kDa bands exhibited rises in $I_{sc}$ of 24.3 and 19.5 $\mu Amp/cm^2$, respectively. The remaining two immunoreactive bands showed no enterotoxic activity.

The observation that convalescent sera from volunteers who were fed wild-type *S. flexneri 2a* contain antibodies that neutralize the enterotoxic activity *S. flexneri 2a* supernatants in Ussing chambers, and that specifically bind to immobilized protein shown to produce such activity, demonstrates that ShET1 is expressed in vivo where it elicits an immune response. Thus, it is likely that this enterotoxin plays a role in the pathogenesis of Shigella diarrhea in humans.

B. N-terminal Sequencing of ShET1

To obtain greater protein mass for sequencing, scale-up of the chromatographic procedure was preformed using Sephacryl S-200 (Pharmacia, Piscataway, N.J.) packed in a calibrated, 4° C. jacketed, 5×100 cm XK 50/100 column (Pharmacia). The 65–75 kDa size fraction was handled as above except that a polyvinylidine diflouridine membrane, Immobilon, Millipore) was substituted for nitrocellulose for electrophoretic transfer. The three protein bands, identified as described above, were excised, extensively rinsed with distilled water and dried. Individual strips bearing the protein bands were then subjected to N-terminal sequencing on an Applied Biosystems model 477A sequencer, as described by Hall et al, *J. Bacteriol.,* 171:6372–6374 (1989). The determined N-terminal sequence data are shown in Table 2 below.

TABLE 2

Preliminary N-terminal amino acid sequence of Shigella enterotoxin 1

| MW of enterotoxic moiety | Proposed A:B subunit ratio[*] | N-terminal amino acid sequence 1[‡] | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 63 kDa | A1:B3 | Ala<br>Asp[§] | Pro<br>Thr | Pro | Val<br>Leu | (SEQ ID NO:3) | | | | | | | | | |
| 53 kDa | A1:B2 | Ala<br>Asp | Pro<br>Thr | Pro | Val<br>Leu | (SEQ ID NO:3) | | | | | | | | | |
| 41 kDa | A1:B1 | Ala<br>Asp | Pro<br>Thr | Pro | Val | Pro<br>Glu | Ile | Asn | Pro | Ala<br>Phe | Xaa | Pro<br>Arg | Ile<br>Arg | Xaa | Arg* |

[*]assuming an A subunit size of about 30 kDa and a B subunit size of about 11 kDa
[‡]sequencing cycle number
[§]Duplicate amino acid signals detected for samples at positions indicated
*(SEQ ID NO:4)

As shown in Table 2 above, a definitive extended sequence could not be determined from the material available for any of the three bands. However, the identical putative amino acid sequence was found for the first four residues of all three bands. Moreover, the data derived suggested that two distinct N-termini were being identified. Notably, this was consistent for all three bands examined.

The University of Wisconsin package (Genetics Computer Group, Madison, Wis.) (Devereux et al, Nucleic Acids Res., 12:387–395 (1984)), data bases containing known protein sequences and untranslated DNA sequences were perused to identify those with potential amino acid homology to the putative N-terminal sequences acquired from the above samples. GenBank release 75.0 and PIR Protein 35.0 were also examined using the TFASTA and WORD-SEARCH programs. No apparent regions of extensive alignment were found to exist. In addition, no substantial homology to known bacterial toxins was detected.

The common A:$B_n$ active:binding unit motif frequently encountered in bacterial enterotoxins, including cholera toxin (CT) (LoSpalluto et al, *Biochem. Biophys. Acta,* 257:158–166 (1972)), heat-labile enterotoxin (LT) of enterotoxigenic *E. coli* (Clements et al, *Infect. Immun.,* 38:806–809 (1982)) and Shiga toxin of *S. dysenteriae* 1 (Olsnes et al, *J. Biol. Chem.,* 256:8732–8738 (1981); and Seidah et al, *J. Biol. Chem.,* 261:13928–13931 (1986)), may be reflected in the above data. That is, as proposed in Table 2, the apparent molecular sizes of active material are consistent with such stoichiometries based upon the sizes of the A (28–32 kDa) and B (7.7–11 kDa) subunits of the previously identified enterotoxins. By extension, a holotoxin consistent with a size of 65–75 kDa and an A1:B4 structure would be predicted by these conventions. These tentative configurations also satisfy the usual requirements for both a binding and an active domain that allow the enterotoxin to attach and gain entrance to enterocytes and to initiate events that culminate in intestinal secretion.

EXAMPLE 4

Gene Sequencing of Enteroinvasive *E. coli* Enterotoxin

A genetic approach was employed to identify and clone the enterotoxin from enteroinvasive *E. coli.* More specifically, TnphoA insertion mutants were generated in EIEC strain EI-37 (0136:NM) (Fasano et al, *Infect. Immun.,* 58:3717–3723 (1991)) as described by Taylor et al, *J. Bacteriol.,* 171:1870–1978 (1989). The resulting TnphoA insertion mutants were screened for increased expression of alkaline phosphatase in low iron L-agar (containing 30 μg/ml of EDDA) compared with standard L-agar. As a result, nine insertion mutants with increased expression of alkaline phosphatase were identified.

The supernatants from the resulting nine TnphoA insertion mutants were then tested in Ussing chambers as described above, and two of the mutants were found to have significantly less enterotoxic activity, as defined by changes in $I_{sc}$, than the wild-type parent, suggesting that the phoA gene was inserted into the open reading frame that encodes enterotoxic activity.

Figure 5:
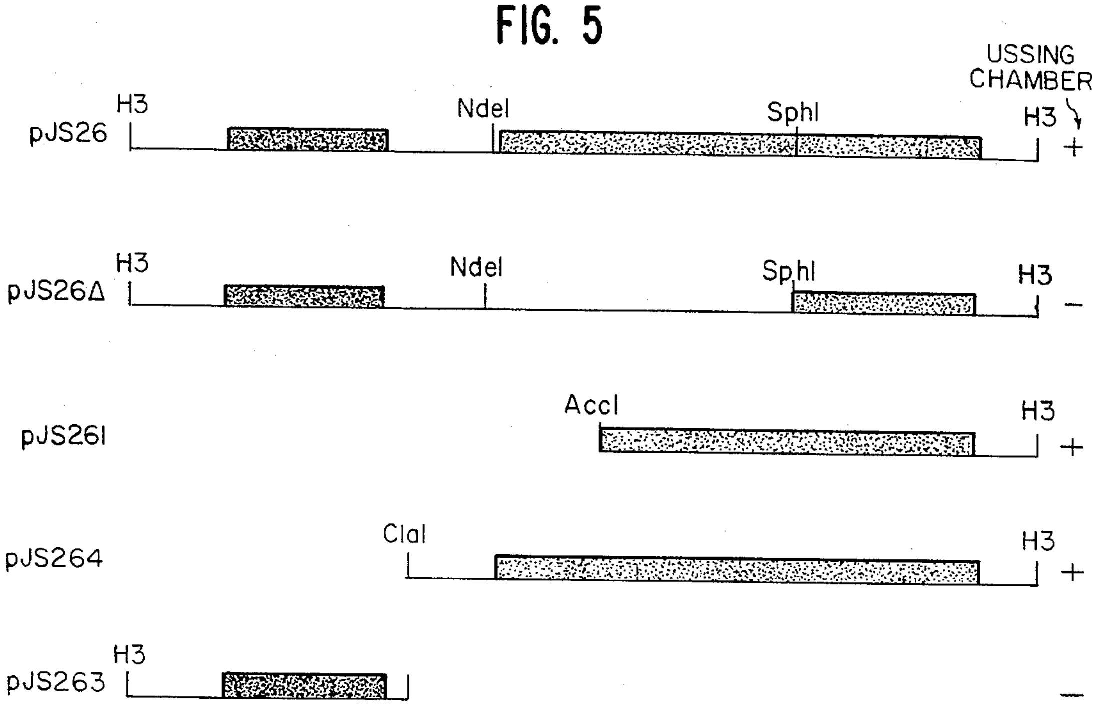
FIG. 5 shows a restriction map of the fragments in pJS26 which contains the tie gene, as well as restriction maps for the relevant portions of plasmids derived from pJS26.

DNA was then purified from the two mutants, and the purified DNA was digested with BamHI. The resulting DNA fragments, which flank the TnphoA insertions, were cloned into the BamHI site of vector pBluescript Sk+/– (Stratagene, La Jolla, Calif.). Then, the cloned DNA was hybridized against a pHC79 cosmid library of EIEC strain EI-34 (Fasano et al, *Infect. Immun.,* 58.:3717–3723 (1991)). The flanking DNA sequences from one of the two TnphoA insertion mutants were found to be homologous to nine cosmid clones. Random subcloning of these cosmid clones into pBluescript Sk+/– led to the identification of a 2.8 kb HindIII fragment which was found to encode enterotoxin activity in Ussing chambers. This fragment, when cloned into the HindIII site of pBluescript Sk+/–, gave rise to pJS26 (FIG. 5). DH5α (Gibco/BRL Life Technologies, Gaithersberg, Md.) was transformed with pJS26, and found to confer reproducible increases in $I_{sc}$ in Ussing chambers.

The 2.8 kb HindIII fragment was manually sequenced, and two potential open reading frames (orf's), encoding predicted peptides of 62.8 kDa and 16.1 kDa were found (FIG. 5).

The 2.8 kb HindIII fragment was digested with ClaI and subcloned into HindIII- and ClaI-digested pBluescript Sk+/–, to give rise to pJS264, which contained only the 62.8 kDa orf (FIG. 5). DH5α transformed with pJS264 exhibited rises in $I_{sc}$ in Ussing chambers similar to that found with the entire 2.8 kb HindIII fragment. This orf, whose DNA sequence, along with the determined amino acid sequence are shown in FIGS. 6A–6C (SEQ ID NO:1), was therefore designated tie (for "toxin invasive *E. coli*").

The 2.8 kb HindIII fragment was also digested with ClaI and subcloned into HindIII- and ClaI-digested pBluescript Sk+/–, to give rise to pJS263, which contained only the 16.1 kDa orf (FIG. 5). DH5α transformed with pJS264 did not elicit rises in $I_{sc}$ in Ussing chambers.

A GenBank search for amino acid homology of the translated orf's revealed no significant identity to any known prokaryotic sequences.

The 2.8 kb HindIII fragment containing the tie gene was then digested with AccI and cloned into DH5α so as to obtain pJS261 (FIG. 5), which was then used to transform DH5α. The resulting transformant was also found to express enterotoxic activity when tested in Ussing chambers as described above.

In order to gauge the effect of the tie gene on secretory activity, a deletion mutation was constructed by digesting the tie gene in pJS26 with NdeI and SphI. The resulting plasmid was designated pJS26a (FIG. 5). This plasmid lacked the first two-thirds of the N-terminus of the open reading frame. This plasmid was then used to transform DH5α, and tested in Ussing chambers as described above. The supernatant obtained from the pJS26Δ transformants elicited less response in the Ussing chamber assay when compared to pJS26, confirming that tie gene is the EIET structural gene.

Thus, unlike ShET1, which as discussed above is believed to be composed of A and B subunits, EIET is a single molecule.

EXAMPLE 5

Gene Sequencing of Shigella Enterotoxin 2 (ShET2)

As discussed above, Shigella and EIEC share some similarities. Thus, the orf containing the gene encoding the EIEC enterotoxin shown in FIGS. 6A–6D (SEQ ID NO:1) was used as a probe to determine whether Shigella has similar DNA sequences.

More specifically, purified genomic DNA was obtained from each of *S. flexneri* 5a M4243 and *S. flexneri* 2a M4243avir, digested with SalI, another screened for hybridization with the tie gene. The DNA-DNA hybridization showed the presence of a single 3.5 kb band in genomic DNA from the wild-type strain, but not from the plasmid-cured derivative. This result suggests that the homologous DNA is located on the invasiveness plasmid.

The 3.5 kb SalI fragment was identified on the *S. flexneri* 2a M4243 plasmid by PCR using the following oligonucleotide primers that hybridize to the tie gene (CAGTGTAT- CACCACGAG (SEQ ID NO:13); and AAATTATCTA-CAGTCAG (SEQ ID NO:14)), and sequenced using an automated sequencer. The resulting DNA sequence, along with the determined amino acid sequence are shown in FIGS. 7A–7D (SEQ ID NO:2). As shown in FIGS. 7A–7D (SEQ ID NO:2), this fragment was found to contain a 1595 bp open reading frame and has at least 99% homology to the EIET gene. This Shigella gene encodes for a protein of a predicted MW of 63 kDa, and a pI of 6.36. No leader peptide was identified. The analysis of the peptide structure revealed three possible membrane spanning domains (amino acid positions 120–140, 260–300 and 480–520) and five cysteine residues. A predicted ribosome binding site is found at nucleotide positions 290–293. When the translation of this open reading frame was compared to the N-terminal sequence of ShET1 shown in Table 2, no homologies were found, suggesting that this gene, located on the *S. flexneri* 2*a* M4243 plasmid, encodes for a toxin (hereinafter named "ShET2") which is distinct from ShET1, but substantially identical to EIET.

Due to the similarity between the EIET gene and the ShET2 gene, it is evident that the gene located on *S. flexneri* 2*a* M4243 plasmid, i.e., that hybridized with EIET gene probe, is the ShET2 structural gene.

EXAMPLE 6

Use of EIEC Enterotoxin Gene as a DNA Probe

The tie gene was used as a DNA probe and hybridized against a collection of EIEC and Shigella strains under high stringency by the colony blot method. The results are shown in Table 3.

TABLE 3

Prevalence of tie Gene in *E. coli* and Shigella
Colony Blot Hybridization with tie Probe

| Category | Positive | Negative | % Positive |
|---|---|---|---|
| Shigella | 27 | 7 | 80% |
| EIEC | 60 | 20 | 75% |
| Other *E. coli* | 0 | 110 | 0% |

As shown in Table 3 above, the tie-homologous sequences are present in 80% (27/34) of Shigella strains, including members of all four Shigella species (*flexneri, boydii, sonnei* and *dysenteriae*), and 75% of EIEC. None of 110 *E. coli* other than EIEC carried homologous sequences.

EXAMPLE 7

Gene Sequencing of Shigella Enterotoxin 1 (ShET1)

A colony immunoblot technique was utilized to clone the ShET1 gene (set1) using the rabbit polyclonal antibodies described in Example 2.

More specifically, a library of genomic DNA obtained from the plasmid-cured derivative of *S. flexneri* 2*a* strain 2457T, designated as strain 2457TA (the Walter Reed Army Institute of Research), was obtained by partial digestion with Sau3A. The resulting 5 to 10 kb fragments were purified by GeneClean, and then Sau3A DNA termini were partially filled in with dATP and dGTP in a Klenow reaction.

Separately, the cos ends of undigested λZAPII vector (Stratagene, La Jolla, Calif.) were ligated, the vector digested with XhoI and the resulting termini partially filled in with dCTP and dTTP. This resulted in compatible ends between the vector and genomic inserts, but not between themselves.

The compatible ends of the genome fragments and the vector were ligated and packaged using the Gigapack II Gold packing extract (Stratagene) system following the procedures recommended by the manufacturer. The resulting λZAPII::2457TA library was titrated in *E. coli* strain XL1-Blue MRF' (Stratagene) to obtain a concentration of 100 plaques/100 mm plate. Next, the plaques were blotted with IPTG-saturated nitrocellulose filters using the procedures for immunological screening of expression of bacteriophage λ vector libraries described by Sambrook et al, *Molecular Cloning. A Laboratory Manual,* Second Edition, Cold Spring Harbor Laboratory Press (1989).

Then, 40 filters (approx. $4\times10^3$ plaques) were screened with the rabbit polyclonal antiserum described in Example 2, and six plaques were found to be strongly positive. These plaques were harvested, and pBluescript Sk+/− containing the corresponding 2457TA DNA inserts were excised from the λZAPII vector using the ExAssist/SOLR system (Stratagene) using procedures recommended by the manufacturer.

The resulting pBluescript Sk+/− was used to infect DH5α, and 24 single colonies derived from each immunoblot-positive plaque were grown in 300 ml of $Fe^{++}$-depleted LB medium with 100 μg/ml ampicillin in 96-well microtiter plates and cultured at 37° C. for 48 h. The supernatants of these cultures were then passed by gravity through nitrocellulose paper in a 96-well manifold (Biorad), and immunoblotted with the above described rabbit antiserum. The supernatants from clones derived from one positive plaque were found to be strongly reactive.

Figure 8:
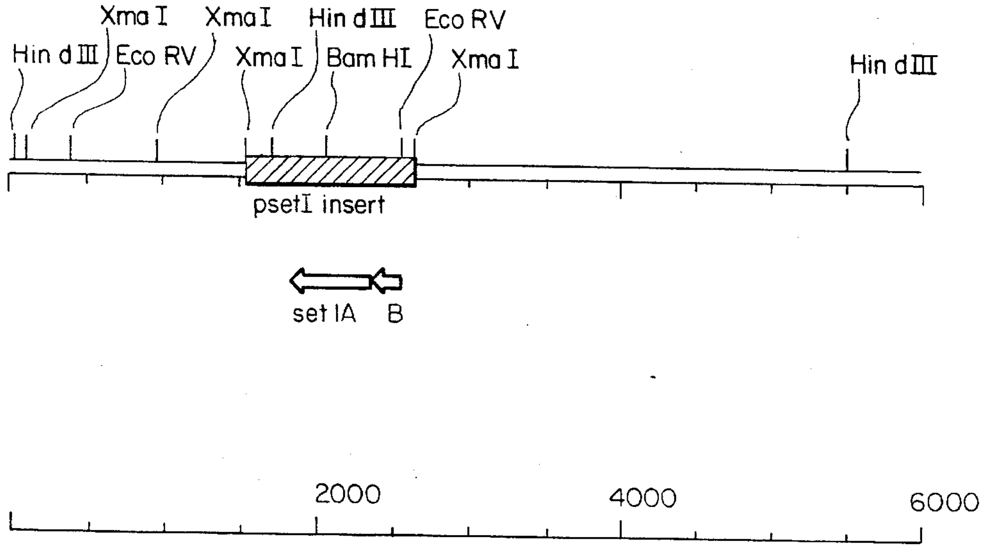
FIG. 8 shows the restriction map of the fragment in pF9-1-90 which contains the ShET1 gene.

Filter-sterilized supernatants from 6 arbitrarily-selected of these strongly reactive clones were tested on rabbit ileal mucosa in Ussing chambers. One of these supernatants induced $I_{sc}$ changes (58.7+/−7.9 $\mu Amp/cm^2$) significantly higher then DH5α (17.9+/−7.3 $\mu Amp/cm^2$) negative control supernatants and equivalent to 2457TA supernatant (38.8+/−10.1 $\mu Amp/cm^2$). The plasmid contained in this clone, designated pF9-1-90, was purified, mapped and a 6.0 kb DNA insert was found (see FIG. 8). Western immunoblots of supernatants from clones containing plasmid pF9-1-90 showed the expression of similar banding pattern present in 2457TA, but not in the host DH5α (pBluscript Sk+/−) alone.

Using the multiple restriction enzymes found in the polylinker of pBluscript Sk+/− as reference, various segments of the 6.0 kb insert were subcloned in the same vector. Supernatants from clones containing segments of various sizes were tested in Ussing chambers and immunoblots.

Single strand sequencing of a selected genomic insert in pF9-1-90 was performed by automated fluorescent sequencing (Applied Biosystems DNA sequencer Model 373A, Foster City, Calif.). The complementary DNA strand was sequenced by chain-termination sequencing using the Sequenase Version 2.0 DNA sequencing kit (USB, Cleveland, Ohio). Chain-termination sequencing was used as well to identify and determine the orientation of the set1 genes in pset1, described below.

Sequencing analysis of a 3.0 kb DNA segment downstream of the promoter T7 in pF9-1-90 revealed two open reading frames (orf), of respectively 146 bp (set1B) and 574 bp (set1A), in the same orientation, separated by only 6.0 bp (FIGS. 9A–9B; SEQ ID NO:15).

Surprisingly, the ShET1 predicted amino acid sequence based on the DNA sequence shown in FIGS. 9A–9B did not corrspond to the N-terminal amino acid sequence shown in Table 2. This confirms the difficulty in cloning the ShET1 gene.

The predicted molecular weights (MW) of the protein molecules encoded by these orfs are of approximately 7.0 kDa and 20 kDa for set1B and set1A, respectively. The finding of a 55 kDa protein in the immunoblot experiments described below supports the concept of an $A_1$:$B_5$ configuration for the holotoxin, where the A subunit is 20 kDa and each individual B subunit is 7.0 kDa. The set1B gene has an upstream promoter governing the transcription of both the set1B and set1A genes.

Analysis of the amino acid sequence of set1B revealed a peptide structure with a predicted signal sequence. Comparison of the predicted protein with the EMBL/GenBank library of sequences did not show significant homologies among prokariotic or eukariotic sequences at the amino acid or nucleotide level. The set1A gene has its own Shine Delgarno sequence 15 bp upstream the initiation codon. The predicted amino acid sequence of set1A also features a putative signal sequence. Comparison of this orf with the EMBL/GenBank did not reveal significant homologies with known sequences.

A 1,093 bp fragment containing the set1 orfs (with an upstream segment of 98 bp) was obtained by digesting the 6.0 Kb insert in pF9-1-90 with XmaI and cloning it in pBluescript SK+/–. The plasmid so obtained, named pset1, was transformed into DH5α. DH5α(pset1) supernatant was then immunoblotted as described above, and tested in Ussing chambers for enterotoxic activity.

Immunoblot of the $Fe^{++}$-depleted supernatant from the DH5α(pset1) culture revealed the expression of the 55 kDa protein band detected in *S. flexneri* 2*a* strain 2457TA and pF9-1-90 supernatants, but not in the DH5α negative control. DH5α(pset1) supernatant induced an increase in $I_{sc}$ when tested in Ussing chambers (79.18+/–14.1 μAmp/$cm^2$; n=6) higher than that seen with *S. flexneri* 2*a* wild-type strain 2457TA (38.80+/–7.6 μAmp/$cm^2$; n=6) and DH5α(pF9-1-90) (53.63+/–11.3 μAmp/$cm^2$; n=8). All ShET1-containing supernatants tested in Ussing chambers showed a high increase of $I_{sc}$ as compared to the changes induced by supernatants obtained from the DH5α(pBluescript SK+/–) negative control (10.18+/8.5 μAmp/$cm^2$; n=7; p<0.01). The enterotoxic effect was proportional to the level of expression of ShET1 (pset1>pF9-1-90>2457TA), suggesting a dose-response relationship for the toxicity of ShET1.

EXAMPLE 8

Construction of the Attenuated *S. flexneri* Strain CVD1203

*S. flexneri* 2*a* strain 2457T (Kotloff et al, *Infect. Immun.* 60:2218–2224 (1992)), known to be virulent based on experimental challenge studies in adult volunteers, was selected as the wild-type parent to be attenuated by introduction of a deletion in both the aroA and VirG genes.

More specifically, the aroA gene (Duncan et al, *FEBS,* 170:59–63 (1984)) was subjected to polymerase chain reactions in a Programmable Thermal Controller unit, using Taq polymerase and buffer obtained from Promega to obtain a deletion of 201 nucleotides in the aroA gene, which corresponds to a deletion of amino acids 168–231 of the encoded enzyme. In particular, the 5' end of the aroA gene was amplified with the upstream primer (TAATCGAATTCATGGAATCCCTGACGTTA) (SEQ ID NO:5) so as to introduce an EcoRI site, and with the down stream primer (GGTACCCCCAATATTAGGGCCATCAACGTCAACGTTGCCGCC) (SEQ ID NO:6) so as to introduce KpnI and SspI sites. The 3' end of the aroA gene was amplified with the upstream primer (AATATTGGGGGTACCGGTACTTATTTGGTCGAAGGCGATGCA) (SEQ ID NO:7) so as to introduce SspI and KpnI sites, and with the downstream primer (TGATAAGTCGACTCAGGCTGCCTGGCTAAT) (SEQ ID NO:8) so as to introduce a SalI site. Both segments were amplified for 30 cycles of 1 min at 94° C. 2 min at 50° C. and 4 min at 72° C.

In a second PCR reaction, the 5' and 3' segments were fused, and the resulting fusion product was amplified in the same reaction. In this reaction, the given homologous regions (SspI-KpnI) annealed, effectively fusing the 5' and 3' segments, which at that time may have acted as their own primers and/or templates for the Taq polymerase, depending upon which stands of DNA were annealed. To facilitate this fusion, the first 15 cycles had an annealing temperature slope (1° C./8 sec from 40° C. to 50° C.+50° C. for 2 min), followed by 15 cycles with an annealing temperature of 55° C. in which the new ΔaroA gene was amplified. The ΔaroA gene of Shigella was cloned into the EcoRI and SalI sites of the temperature-sensitive vector pIB307 (Blomfield et al, *Mol., Microbiol.,* 5:1447–1457 (1991)) to give rise to pIB307::ΔaroA. pIB307::ΔaroA was electroporated into *E. coli* DH5α and grown at 30° C. In a second step, the sacB-neomycin$^R$ segment of pIB279 (Blomfield et al, *Mol., Microbiol.,* 5:1447–1457 (1991)) was transferred into the BamHI polylinker site of pIB307::ΔaroA, and the resultant plasmid, designated pFJ201, was introduced into DH5α by electroporation, and incubated at 30° C.

pFJ201 was electroporated into *S. flexneri* 245T to achieve allelic exchange in the wild-type strain. Co-integates representing a single homologous recombination were readily obtained. Using counter selection (Aro-sucrose plates at 30° C.), a clone was identified that had characteristics of the double homologous recombination event, i.e., representing allelic exchange of ΔaroA for aroA in the chromosome. This clones was kanamycin-sensitive, Congo red-positive, agglutinated with *S. flexneria* 2*a* antiserum, and was unable to grow in Shigella minimum medium (SMM) consisting of 0.4 g NaCl, 8.4 g $K_2HPO_4$, 3.6 g $KH_2PO_4$, 0.8 g $(NH_4)_2SO_4$, 2.5 g glucose, 0.05 g nicotonic acid, 0.05 g aspartic acid, 0.05 g serine and 15 g nobel L-agar. SMM allows one to screen for ΔaroA mutants colonies that cannot synthesize aromatic compounds de novo, and thus require exogenus aromatic compounds in order to grown. PCR of this strain demonstrated that the gene produced harbored a deletion; the wild-type product was 1.2 kb, whereas the product of the clone was 1.0 kb. Confirmation of the deletion was made using a 40 base synthetic oligonucleotide sequence derived from the deleted portion of the gene. The 32P-labelled probe hybridized with wild-type colonies, but not with the clone. This ΔaroA clone was designated CVD1201.1.

Strains ΔaroA CVD 1201.1 and wild-type 2457T were grown shaking at 37° C. in 5.0 ml volumes of SMM that was progressively supplemented with aromatic amino acids (50 mg L-tryptophan, 50 mg L-tyrosine, 50 mg L-phenylalanine), 10 mg ferric ammonium acetate and 10 mg PABA. CVD 1201.1 required the addition of tryosine, tryptophan, phenylalanine and PABA in order to grow.

A deletion of 900 nucleotides in the virG gene (Lett et al, *J. Bacteriol.,* 172:352–359 (1989)), which corresponds to a deletion of amino acids 341–640 of the 120 kDa VirG protein, was obtained by following steps analogous to that used for preparing the ΔaroA mutation. The specific engineered site for this deletion in the 120 kDa protein represents a highly hydrophobic, poorly antigenic portion of the molecule according to the Jameson/Wolf antigenic index (IBI Pustell Sequence Analysis Programs). More specifically, the 5' end of the virG gene was amplified with the upstream primer (GGGGAATTCCAAATTCACAAATTTTTTTGT) (SEQ ID NO:9) so as to introduce an EcoRI site, and with the downstream primer (TCCATGCCATTCATGGAGTATTAATGAATT) (SEQ ID NO:10). The 3' end of the virG gene was amplified with the upstream primer (CTCCATGAATGGCATGGAAAGGCGGAATA) (SEQ ID NO:11), and the downstream primer (CGGGTCGACTCAGAAGGTATATTTCACACCCAA) (SEQ ID NO:12) so as to introduce a SalI site. Amplification and fusion of the virG 5' and 3' segments were performed using the same PCR cycles described above. The resulting new ΔvirG gene was cloned into the EcoRI and SalI sites of the pir-based suicide vector pKTN701 (Hone et al, *Vaccine,* 9:810–816 (1991)), giving rise to pShΔvirG, which was electroporated into *E. coli* strain SY327 (Miller et al, *J. Bacteriol.,* 170:2575–2583 (1983)). The plasmid was then electroporated into strain Sm10λpir (Miller et al, *J. Bacteriol.,* 170:2575–2583 (1983)). Sm10λpir(pShΔvirG) was used to conjugate the deletion cassette into the ΔaroA strain, CVD1201.1.

Suicide vector pShΔvirG was integrated into the virulence plasmid (ΔvirG) loci of the ΔaroA strain, CVD1201.1, to introduce the ΔvirG mutation by homologous recombination, followed by chloramphenicol-sensitive enrichment using the procedures described for Salmonella by Hone et al, *Vaccine,* 9:810–816 (1991).

An antibiotic-sensitive clone representing a putative successful double homologous recombination event was confirmed by PCR, Congo red positivity, agglutination with *S. flexneri* 2*a* antiserum and failure to hybridize with the oligonucleotide probe specific for the deleted sequence.

In this manner the ΔaroA ΔVirG *Shigella flexneri* 2*a* mutant, CVD1203 (ATCC No. 55556), was isolated.

The 120 kDa VirG protein was not detected in immunoblots using whole cell lysates of CVD1203, and a rabbit antiserum developed against the VirG peptide (Ile 359—Cys 375) representing a fraction of ΔVirG within the deleted portion of ΔVirG. However, an 85 kDa band was detected when rabbit antiserum against another VirG peptide (Leu 55—Thr 73), representing a portion of ΔVirG that it expressed in CVD1203, was used in the immunoblot.

CVD1203, like its wild-type parent, grow on enteric media, which contain sufficient PABA and aromatic amino acids, and manifest a typical acid butt/alkaline slant reaction with $H_2S$ or gas 18–24 h after inoculation of triple sugar iron agar slants. A silver-strained SDS-PAGE of LPS from strains 2457T and CVD1203 demonstrated the identity of the LPS pattern. Similarly, a Western immunoblot of LPS from CVD1203 and 2457T that reacted with human antisera to *Shigella flexneri 2a* 2457T showed identical bands irrespective of the source of the LPS preparation. Water extracts of CVD1203 and 2457T exhibited identical single bands on Western immunoblots with monoclonal antibodies to either IpaB (42 kDa) or to IpaC (62 kDa). Using anti-IpaC monoclonal antibody, dot immunoblots of serial dilutions of the two extracts containing equal amounts of protein demonstrated the same endpoints, indicating that both strains produced the same amount of IpaC.

While the invention has been described in detail, and with reference to specific embodiments thereof, it will be apparent to one of ordinary skill in the art that various changes and modifications can be made therein without departing from the spirit and scope thereof.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 2008 base pairs
( B ) TYPE: nucleic acid
( C ) STRANDEDNESS: single
( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
( A ) ORGANISM: Enteroinvasive E. coli
( B ) STRAIN: EI-37 (0136:NM)

( x i ) SEQUENCE DESCRIPTION: SEQ ID NO:1:

```
ATCGATATAT TGTTTATTGT CAGTATGGCT CAATGTGATA ATAGTTGGAA AGTTTGATGG     60
GTTTCGCCCC GTTGTAGCGG TAGTCGACCC CGTTGTAGCG GTAGTCGAGC TGGAAGGTCT    120
TCAGGCACTG CTTACAGCGA TAGAGCAGCC CCCCAGAACT GGAATGGCCG TTCCGATACC    180
CCCCTGAGTT TCAGAGTAAC GGGGACAAAC CACATCAATC TTTGCCATCA ATCATCCAAA    240
GGGCAAAGAG TACAACAACA CTAAGTCTGC GTCACAACCC ATCAATGAAA GGAATATATA    300
```

-continued

```
CAT ATG CCA TCA GTA AAT TTA ATC CCA TCA AGG AAA ATA TGT TTG CAA   348
    Met Pro Ser Val Asn Leu Ile Pro Ser Arg Lys Ile Cys Leu Gln
    1               5                   10                  15

AAT ATG ATA AAT AAA GAC AAC GTC TCT GTT GAG ACA ATC CAG TCT CTA   396
Asn Met Ile Asn Lys Asp Asn Val Ser Val Glu Thr Ile Gln Ser Leu
                20                  25                  30

TTG CAC TCA AAA CAA TTG CCA TAT TTT TCT GAC AAG AGG AGT TTT TTA   444
Leu His Ser Lys Gln Leu Pro Tyr Phe Ser Asp Lys Arg Ser Phe Leu
            35                  40                  45

TTA AAT CTA AAT TGC CAA GTT ACC GAT CAC TCT GGA AGA CTT ATT GTC   492
Leu Asn Leu Asn Cys Gln Val Thr Asp His Ser Gly Arg Leu Ile Val
        50                  55                  60

TGT CGA CAT TTA GCT TCC TAC TGG ATA GCA CAG TTT AAC AAA AGT AGT   540
Cys Arg His Leu Ala Ser Tyr Trp Ile Ala Gln Phe Asn Lys Ser Ser
    65                  70                  75

GGT CAC GTG GAT TAT CAT CAC TTT GCT TTT CCG GAT GAA ATT AAA AAT   588
Gly His Val Asp Tyr His His Phe Ala Phe Pro Asp Glu Ile Lys Asn
80                  85                  90                  95

TAT GTT TCA GTG AGT GAA GAA GAA AAG GCT ATT AAT GTG CCT GCT ATT   636
Tyr Val Ser Val Ser Glu Glu Glu Lys Ala Ile Asn Val Pro Ala Ile
                100                 105                 110

ATT TAT TTT GTT GAA AAC GGT TCA TGG GGA GAT ATT ATT TTT TAT ATT   684
Ile Tyr Phe Val Glu Asn Gly Ser Trp Gly Asp Ile Ile Phe Tyr Ile
            115                 120                 125

TTC AAT GAA ATG ATT TTT CAT TCC GAA AAA AGC AGA GCA CTA GAA ATA   732
Phe Asn Glu Met Ile Phe His Ser Glu Lys Ser Arg Ala Leu Glu Ile
        130                 135                 140

AGT ACA TCA AAT CAC AAT ATG GCA TTA GGC TTG AAG ATT AAA GAA ACT   780
Ser Thr Ser Asn His Asn Met Ala Leu Gly Leu Lys Ile Lys Glu Thr
    145                 150                 155

AAA AAT GGG GGG GAT TTT GTC ATT CAG CTT TAT GAT CCC AAC CAT ACA   828
Lys Asn Gly Gly Asp Phe Val Ile Gln Leu Tyr Asp Pro Asn His Thr
160                 165                 170                 175

GCA ACT CAT TTA CGA GCA GAG TTT AAC AAA TTT AAC TTA GCT AAA ATA   876
Ala Thr His Leu Arg Ala Glu Phe Asn Lys Phe Asn Leu Ala Lys Ile
                180                 185                 190

AAA AAA CTG ACT GTA GAT AAT TTT CTT GAT GAA AAA CAT CAG AAA TGT   924
Lys Lys Leu Thr Val Asp Asn Phe Leu Asp Glu Lys His Gln Lys Cys
            195                 200                 205

TAT GGT CTT ATA TCC GAC GGT ATG TCT ATA TTT GTG GAC AGA CAT ACT   972
Tyr Gly Leu Ile Ser Asp Gly Met Ser Ile Phe Val Asp Arg His Thr
        210                 215                 220

CCA ACA AGC ATG TCC TCC ATA ATC AGA TGG CCT AAT AAT TTA CTT CAC  1020
Pro Thr Ser Met Ser Ser Ile Ile Arg Trp Pro Asn Asn Leu Leu His
    225                 230                 235

CCC AAA GTT ATT TAT CAC GCG ATG CGT ATG GGA TTG ACT GAG CTA ATC  1068
Pro Lys Val Ile Tyr His Ala Met Arg Met Gly Leu Thr Glu Leu Ile
240                 245                 250                 255

CAA AAA GTA ACA AGA GTC GTA CAA CTA TCT GAC CTT TCA GAC AAT ACG  1116
Gln Lys Val Thr Arg Val Val Gln Leu Ser Asp Leu Ser Asp Asn Thr
                260                 265                 270

TTA GAA TTA CTT TTG GCA GCC AAA AAT GAC GAT GGT TTG TCA GGA TTG  1164
Leu Glu Leu Leu Leu Ala Ala Lys Asn Asp Asp Gly Leu Ser Gly Leu
            275                 280                 285

CTT TTA GCT TTA CAA AAT GGG CAT TCA GAT ACA ATC TTA GCA TAC GGA  1212
Leu Leu Ala Leu Gln Asn Gly His Ser Asp Thr Ile Leu Ala Tyr Gly
        290                 295                 300

GAA CTC CTG GAA ACT TCT GGA CTT AAC CTT GAT AAA ACG GTA GAA CTA  1260
Glu Leu Leu Glu Thr Ser Gly Leu Asn Leu Asp Lys Thr Val Glu Leu
    305                 310                 315
```

-continued

CTA ACT GCG GAA GGA ATG GGA GGA CGA ATA TCG GGT TTA TCC CAA GCA 1308
Leu Thr Ala Glu Gly Met Gly Gly Arg Ile Ser Gly Leu Ser Gln Ala
320 325 330 335

CTT CAA AAT GGG CAT GCA GAA ACT ATC AAA ACA TAC GGA AGG CTT CTC 1356
Leu Gln Asn Gly His Ala Glu Thr Ile Lys Thr Tyr Gly Arg Leu Leu
340 345 350

AAG AAG AGA GCA ATA AAT ATC GAA TAC AAT AAG CTG AAA AAT TTG CTG 1404
Lys Lys Arg Ala Ile Asn Ile Glu Tyr Asn Lys Leu Lys Asn Leu Leu
355 360 365

ACC GCT TAT TAT TAT GAT GAA GTA CAC AGA CAG ATA CCT GGA CTA ATG 1452
Thr Ala Tyr Tyr Tyr Asp Glu Val His Arg Gln Ile Pro Gly Leu Met
370 375 380

TTT GCT CTT CAA AAT GGA CAT GCA GAT GCT ATA CGC GCA TAC GGT GAG 1500
Phe Ala Leu Gln Asn Gly His Ala Asp Ala Ile Arg Ala Tyr Gly Glu
385 390 395

CTC ATT CTT AGC CCC CCT CTC CTC AAC TCA GAG GAT ATT GTA AAT TTG 1548
Leu Ile Leu Ser Pro Pro Leu Leu Asn Ser Glu Asp Ile Val Asn Leu
400 405 410 415

CTG GCC TCA AGG AGA TAT GAC AAT GTT CCC GGA CTT CTG TTA GCA TTG 1596
Leu Ala Ser Arg Arg Tyr Asp Asn Val Pro Gly Leu Leu Leu Ala Leu
420 425 430

AAT AAT GGA CAG GCT GAT GCA ATC TTA GCT TAT GGT GAT ATC TTG AAT 1644
Asn Asn Gly Gln Ala Asp Ala Ile Leu Ala Tyr Gly Asp Ile Leu Asn
435 440 445

GAG GCA AAA CTT AAC TTG GAT AAA AAA GCA GAG CTG TTA GAA GCG AAA 1692
Glu Ala Lys Leu Asn Leu Asp Lys Lys Ala Glu Leu Leu Glu Ala Lys
450 455 460

GAT TCT AAT GGT TTA TCT GGA TTG TTT GTA GCC TTG CAT AAT GGA TGT 1740
Asp Ser Asn Gly Leu Ser Gly Leu Phe Val Ala Leu His Asn Gly Cys
465 470 475

GTA GAA ACA ATT ATT GCT TAT GGG AAA ATA CTT CAC ACT GCA GAC CTT 1788
Val Glu Thr Ile Ile Ala Tyr Gly Lys Ile Leu His Thr Ala Asp Leu
480 485 490 495

ACT CCA CAT CAG GCA TCA AAA TTA CTG GCA GCA GAA GGC CCA AAT GGG 1836
Thr Pro His Gln Ala Ser Lys Leu Leu Ala Ala Glu Gly Pro Asn Gly
500 505 510

GTA TCT GGA TTA ATT ATA GCT TTT CAA AAT AGG AAT TTT GAG GCA ATA 1884
Val Ser Gly Leu Ile Ile Ala Phe Gln Asn Arg Asn Phe Glu Ala Ile
515 520 525

AAA ACT TAT ATG GGA ATA ATA AAA AAT GAA AAT ATT ACA CCT GAA GAA 1932
Lys Thr Tyr Met Gly Ile Ile Lys Asn Glu Asn Ile Thr Pro Glu Glu
530 535 540

ATA GCA GAA CAC TTG GAC AAA AAA AAT GGA AGT GAT TTT CTA GAA ATT 1980
Ile Ala Glu His Leu Asp Lys Lys Asn Gly Ser Asp Phe Leu Glu Ile
545 550 555

ATG AAG AAT ATA AAA AGC TGAATATTAT 2008
Met Lys Asn Ile Lys Ser
560 565

( 2 ) INFORMATION FOR SEQ ID NO:2:

( i ) SEQUENCE CHARACTERISTICS:
( A ) LENGTH: 1722 base pairs
( B ) TYPE: nucleic acid
( C ) STRANDEDNESS: single
( D ) TOPOLOGY: linear ( i i ) MOLECULE TYPE: genomic DNA ( i i i ) HYPOTHETICAL: NO ( i v ) ANTI-SENSE: NO -continued ( v i ) ORIGINAL SOURCE:
( A ) ORGANISM: Shigella flexneri 2a
( B ) STRAIN: M4243

( x i ) SEQUENCE DESCRIPTION: SEQ ID NO:2:

```
ACCCATCAAT GAAAGGAATA TATA CAT ATG CCA TCA GTA AAT TTA ATC CCA        51
                               Met Pro Ser Val Asn Leu Ile Pro
                               1               5

TCA AGG AAA ATA TGT TTG CAA AAT ATG ATA AAT AAA GAC AAC GTC TCT       99
Ser Arg Lys Ile Cys Leu Gln Asn Met Ile Asn Lys Asp Asn Val Ser
    10                  15                  20

GTT GAG ACA ATC CAG TCT CTA TTG CAC TCA AAA CAA TTG CCA TAT TTT      147
Val Glu Thr Ile Gln Ser Leu Leu His Ser Lys Gln Leu Pro Tyr Phe
25                  30                  35                  40

TCT GAC AAG AGG AGT TTT TTA TTA AAT CTA AAT TGC CAA GTT ACC GAT      195
Ser Asp Lys Arg Ser Phe Leu Leu Asn Leu Asn Cys Gln Val Thr Asp
                45                  50                  55

CAC TCT GGA AGA CTT ATT GTC TGT CGA CAT TTA GCT TCC TAC TGG ATA      243
His Ser Gly Arg Leu Ile Val Cys Arg His Leu Ala Ser Tyr Trp Ile
            60                  65                  70

GCA CAG TTT AAC AAA AGT AGT GGT CAC GTG GAT TAT CAT CAC TTT GCT      291
Ala Gln Phe Asn Lys Ser Ser Gly His Val Asp Tyr His His Phe Ala
        75                  80                  85

TTT CCG GAT GAA ATT AAA AAT TAT GTT TCA GTG AGT GAA GAA GAA AAG      339
Phe Pro Asp Glu Ile Lys Asn Tyr Val Ser Val Ser Glu Glu Glu Lys
    90                  95                  100

GCT ATT AAT GTG CCT GCT ATT ATT TAT TTT GTT GAA AAC GGT TCA TGG      387
Ala Ile Asn Val Pro Ala Ile Ile Tyr Phe Val Glu Asn Gly Ser Trp
105                 110                 115                 120

GGA GAT ATT ATT TTT TAT ATT TTC AAT GAA ATG ATT TTT CAT TCC GAA      435
Gly Asp Ile Ile Phe Tyr Ile Phe Asn Glu Met Ile Phe His Ser Glu
                125                 130                 135

AAA AGC AGA GCA CTA GAA ATA AGT ACA TCA AAT CAC AAT ATG GCA TTA      483
Lys Ser Arg Ala Leu Glu Ile Ser Thr Ser Asn His Asn Met Ala Leu
            140                 145                 150

GGC TTG AAG ATT AAA GAA ACT AAA AAT GGG GGG GAT TTT GTC ATT CAG      531
Gly Leu Lys Ile Lys Glu Thr Lys Asn Gly Gly Asp Phe Val Ile Gln
        155                 160                 165

CTT TAT GAT CCC AAC CAT ACA GCA ACT CAT TTA CGA GCA GAG TTT AAC      579
Leu Tyr Asp Pro Asn His Thr Ala Thr His Leu Arg Ala Glu Phe Asn
    170                 175                 180

AAA TTT AAC TTA GCT AAA ATA AAA AAA CTG ACT GTA GAT AAT TTT CTT      627
Lys Phe Asn Leu Ala Lys Ile Lys Lys Leu Thr Val Asp Asn Phe Leu
185                 190                 195                 200

GAT GAA AAA CAT CAG AAA TGT TAT GGT CTT ATA TCC GAC GGT ATG TCT      675
Asp Glu Lys His Gln Lys Cys Tyr Gly Leu Ile Ser Asp Gly Met Ser
                205                 210                 215

ATA TTT GTG GAC AGA CAT ACT CCA ACA AGC ATG TCC TCC ATA ATC AGA      723
Ile Phe Val Asp Arg His Thr Pro Thr Ser Met Ser Ser Ile Ile Arg
            220                 225                 230

TGG CCT GAT AAT TTA CTT CAC CCC AAA GTT ATT TAT CAC GCG ATG CGT      771
Trp Pro Asp Asn Leu Leu His Pro Lys Val Ile Tyr His Ala Met Arg
        235                 240                 245

ATG GGA TTG ACT GAG CTA ATC CAA AAA GTA ACA AGA GTC GTA CAA CTA      819
Met Gly Leu Thr Glu Leu Ile Gln Lys Val Thr Arg Val Val Gln Leu
    250                 255                 260

TCT GAC CTT TCA GAC AAT ACG TTA GAA TTA CTT TTG GCA GCC AAA AAT      867
Ser Asp Leu Ser Asp Asn Thr Leu Glu Leu Leu Leu Ala Ala Lys Asn
265                 270                 275                 280

GAC GAT GGT TTG TCA GGA TTG CTT TTA GCT TTA CAA AAT GGG CAT TCA      915
Asp Asp Gly Leu Ser Gly Leu Leu Leu Ala Leu Gln Asn Gly His Ser
```

-continued

```
                285                     290                     295

GAT ACA ATC TTA GCA TAC GGA GAA CTC TTG GAA ACT TCT GGA CTT AAC     963
Asp Thr Ile Leu Ala Tyr Gly Glu Leu Leu Glu Thr Ser Gly Leu Asn
            300                 305                 310

CTT GAT AAA ACG GTA GAA CTA CTA ACT GCG GAA GGA ATG GGA GGA CGA    1011
Leu Asp Lys Thr Val Glu Leu Leu Thr Ala Glu Gly Met Gly Gly Arg
        315                 320                 325

ATA TCG GGT TTA TCC CAA GCA CTT CAA AAT GGG CAT GCA GAA ACT ATC    1059
Ile Ser Gly Leu Ser Gln Ala Leu Gln Asn Gly His Ala Glu Thr Ile
    330                 335                 340

AAA ACA TAC GGA AGG CTT CTC AAG AAG AGA GCA ATA AAT ATC GAA TAC    1107
Lys Thr Tyr Gly Arg Leu Leu Lys Lys Arg Ala Ile Asn Ile Glu Tyr
345                 350                 355                 360

AAT AAG CTG AAA AAT TTG CTG ACC GCT TAT TAT TAT GAT GAA GTA CAC    1155
Asn Lys Leu Lys Asn Leu Leu Thr Ala Tyr Tyr Tyr Asp Glu Val His
                365                 370                 375

AGA CAG ATA CCC GGA CTA ATG TTT GCT CTT CAA AAT GGA CAT GCA GAT    1203
Arg Gln Ile Pro Gly Leu Met Phe Ala Leu Gln Asn Gly His Ala Asp
            380                 385                 390

GCT ATA CGC GCA TAC GGT GAG CTC ATT CTT AGC CCC CCT CTC CTC AAC    1251
Ala Ile Arg Ala Tyr Gly Glu Leu Ile Leu Ser Pro Pro Leu Leu Asn
        395                 400                 405

TCA GAG GAT ATT GTA AAT TTG CTG GCC TCA AGG AGA TAT GAC AAT GTT    1299
Ser Glu Asp Ile Val Asn Leu Leu Ala Ser Arg Arg Tyr Asp Asn Val
    410                 415                 420

CCC GGA CTT CTG TTA GCA TTG AAT AAT GGA CAG GCT GAT GCA ATC TTA    1347
Pro Gly Leu Leu Leu Ala Leu Asn Asn Gly Gln Ala Asp Ala Ile Leu
425                 430                 435                 440

GCT TAT GGT GAT ATC TTG AAT GAG GCA AAA CTT AAC TTG GAT AAA AAA    1395
Ala Tyr Gly Asp Ile Leu Asn Glu Ala Lys Leu Asn Leu Asp Lys Lys
                445                 450                 455

GCA GAG CTG TTA GAA GCG AAA GAT TCT AAT GGT TTA TCT GGA TTG TTT    1443
Ala Glu Leu Leu Glu Ala Lys Asp Ser Asn Gly Leu Ser Gly Leu Phe
            460                 465                 470

GTA GCC TTG CAT AAT GGA TGT GTA GAA ACA ATT ATT GCT TAT GGG AAA    1491
Val Ala Leu His Asn Gly Cys Val Glu Thr Ile Ile Ala Tyr Gly Lys
        475                 480                 485

ATA CTT CAC ACT GCA GAC CTT ACT CCA CAT CAG GCA TCA AAA TTA CTG    1539
Ile Leu His Thr Ala Asp Leu Thr Pro His Gln Ala Ser Lys Leu Leu
    490                 495                 500

GCA GCA GAA GGC CCA AAT GGG GTA TCT GGA TTA ATT ATA GCT TTT CAA    1587
Ala Ala Glu Gly Pro Asn Gly Val Ser Gly Leu Ile Ile Ala Phe Gln
505                 510                 515                 520

AAT AGG AAT TTT GAG GCA ATA AAA ACT TAT ATG AAA ATA ATA AAA AAT    1635
Asn Arg Asn Phe Glu Ala Ile Lys Thr Tyr Met Lys Ile Ile Lys Asn
                525                 530                 535

GAA AAT ATT ACA CCT GAA GAA ATA GCA GAA CAC TTG GAC AAA AAA AAT    1683
Glu Asn Ile Thr Pro Glu Glu Ile Ala Glu His Leu Asp Lys Lys Asn
            540                 545                 550

GGA AGT GAT TTT CTA GAA ATT ATG AAG AAT ATA AAA AGC                1722
Gly Ser Asp Phe Leu Glu Ile Met Lys Asn Ile Lys Ser
        555                 560                 565
```

( 2 ) INFORMATION FOR SEQ ID NO:3:

( i ) SEQUENCE CHARACTERISTICS:
( A ) LENGTH: 4 amino acids
( B ) TYPE: amino acid
( C ) STRANDEDNESS: unknown
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal fragment ( x i ) SEQUENCE DESCRIPTION: SEQ ID NO:3:

Ala Pro Pro Val 4

( 2 ) INFORMATION FOR SEQ ID NO:4:

( i ) SEQUENCE CHARACTERISTICS:
( A ) LENGTH: 14amino acids
( B ) TYPE: amino acid
( C ) STRANDEDNESS: unknown
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal fragment ( x i ) SEQUENCE DESCRIPTION: SEQ ID NO:4:

Ala Pro Pro Val Pro Ile Asn Pro Ala Xaa Pro Ile Xaa Arg 14

( 2 ) INFORMATION FOR SEQ ID NO:5:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:5:

TAATCGAATT CATGGAATCC CTGACGTTA 29

( 2 ) INFORMATION FOR SEQ ID NO:6:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:6:

GGTACCCCCA ATATTAGGGC CATCAACGTC AACGTTGCCG CC 42

( 2 ) INFORMATION FOR SEQ ID NO:7:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: synthetic DNA -continued ( i i i ) HYPOTHETICAL: NO ( i v ) ANTI-SENSE: NO ( x i ) SEQUENCE DESCRIPTION: SEQ ID NO:7:

AATATTGGGG GTACCGGTAC TTATTTGGTC GAAGGCGATG CA 42

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:8:

TGATAAGTCG ACTCAGGCTG CCTGGCTAAT 30

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:9:

GGGGAATTCC AAATTCACAA ATTTTTTTGT 30

( 2 ) INFORMATION FOR SEQ ID NO:10:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:10:

TCCATGCCAT TCATGGAGTA TTAATGAATT 30

( 2 ) INFORMATION FOR SEQ ID NO:11:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO -continued ( x i ) SEQUENCE DESCRIPTION: SEQ ID NO:11:

CTCCATGAAT GGCATGGAAA GGCGGAATA 29

( 2 ) INFORMATION FOR SEQ ID NO:12:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:12:

CGGGTCGACT CAGAAGGTAT ATTTCACACC CAA 33

( 2 ) INFORMATION FOR SEQ ID NO:13:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:13:

CAGTGTATCA CCACGAG 17

( 2 ) INFORMATION FOR SEQ ID NO:14:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:14:

AAATTATCTA CAGTCAG 17

( 2 ) INFORMATION FOR SEQ ID NO:15:

( i ) SEQUENCE CHARACTERISTICS:
( A ) LENGTH: 723 base pairs
( B ) TYPE: nucleic acid
( C ) STRANDEDNESS: single
( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
( A ) ORGANISM: Shigella flexneri 2a
( B ) STRAIN: M4243

-continued ( x i ) SEQUENCE DESCRIPTION: SEQ ID NO:15:

| | | | | | | | | | | | | | | | | |
|---|---|---|---|---|---|---|---|---|---|---|---|---|---|---|---|---|
| ATG | GTT | CAG | CGT | AAT | ATT | CCC | TTC | ATA | CTG | GCT | CCT | GTC | ATT | CAC | GGT | 48 |
| Met | Val | Gln | Arg | Asn | Ile | Pro | Phe | Ile | Leu | Ala | Pro | Val | Ile | His | Gly | |
| 1 | | | | 5 | | | | | 10 | | | | | 15 | | |
| GTC | CGG | GAC | AGA | GGT | ACC | TTC | CTC | CGG | AAT | GAC | ATA | ATT | TCC | TGT | TCC | 96 |
| Val | Arg | Asp | Arg | Gly | Thr | Phe | Leu | Arg | Asn | Asp | Ile | Ile | Ser | Cys | Ser | |
| | | | 20 | | | | | 25 | | | | | 30 | | | |
| GTC | ATT | TTT | ATC | CAC | AAA | TGC | CCT | GTC | ACT | TCC | CAG | TGT | GAT | ATG | GCT | 144 |
| Val | Ile | Phe | Ile | His | Lys | Cys | Pro | Val | Thr | Ser | Gln | Cys | Asp | Met | Ala | |
| | | 35 | | | | | 40 | | | | | 45 | | | | |
| GTT | ATC | CGA | CTT | AAT | GTC | ACT | GTT | CAG | CGA | GGC | GTT | ACG | TGA | AAG | ATG | 192 |
| Val | Ile | Arg | Leu | Asn | Val | Thr | Val | Gln | Arg | Gly | Val | Thr | * | Lys | Met | |
| | 50 | | | | | 55 | | | | | 60 | | | | | |
| GAA | GTC | AGC | GTC | TTT | CAG | CGA | CAG | TGT | TTT | CAT | TGT | AAA | CTG | ACG | GTT | 240 |
| Glu | Val | Ser | Val | Phe | Gln | Arg | Gln | Cys | Phe | His | Cys | Lys | Leu | Thr | Val | |
| 65 | | | | | 70 | | | | | 75 | | | | | 80 | |
| TTC | CCA | GTC | TTT | CTG | GTT | CAG | GCT | GAC | CGG | TGC | ACT | GCC | ACT | GAT | GGA | 288 |
| Phe | Pro | Val | Phe | Leu | Val | Gln | Ala | Asp | Arg | Cys | Thr | Ala | Thr | Asp | Gly | |
| | | | | 85 | | | | | 90 | | | | | 95 | | |
| GGC | ATG | GAT | AAC | CGG | ATG | TCC | CTG | GAA | TAT | CAG | GGT | GCC | ACT | GTC | CTG | 336 |
| Gly | Met | Asp | Asn | Arg | Met | Ser | Leu | Glu | Tyr | Gln | Gly | Ala | Thr | Val | Leu | |
| | | | 100 | | | | | 105 | | | | | 110 | | | |
| ACT | CAG | GGT | ACC | TTC | CGG | CAG | GTT | CAC | GCT | ACC | ATC | AAA | GAT | TAC | CTT | 384 |
| Thr | Gln | Gly | Thr | Phe | Arg | Gln | Val | His | Ala | Thr | Ile | Lys | Asp | Try | Leu | |
| | | 115 | | | | | 120 | | | | | 125 | | | | |
| TCT | TCC | CCC | CGG | CAC | CTG | TGG | AAT | GGC | GAC | ATC | CAT | ATT | CCC | GGT | CAG | 432 |
| Ser | Ser | Pro | Arg | His | Leu | Trp | Asn | Gly | Asp | Ile | His | Ile | Pro | Gly | Gln | |
| | 130 | | | | | 135 | | | | | 140 | | | | | |
| CTG | ACC | ATG | AAA | GAT | AAC | GGG | TTG | TTT | TGC | CCG | CCC | GGC | CAG | GAT | CCT | 480 |
| Leu | Thr | Met | Lys | Asp | Asn | Gly | Leu | Phe | Cys | Pro | Pro | Gly | Gln | Asp | Pro | |
| 145 | | | | | 150 | | | | | 155 | | | | | 160 | |
| ATC | TTT | TAC | TGT | CTG | AAC | TGC | TTT | GTT | TTT | GTT | CAT | GCC | AAC | AAA | CTC | 528 |
| Ile | Phe | Tyr | Cys | Leu | Asn | Cys | Val | Val | Phe | Val | His | Ala | Asn | Lys | Leu | |
| | | | | 165 | | | | | 170 | | | | | 175 | | |
| CCA | CTG | AGC | CGG | ATC | ATT | CAG | GCT | GTT | CCC | CCA | CAG | AGT | GTT | ACC | ATA | 576 |
| Pro | Leu | Ser | Arg | Ile | Ile | Gln | Ala | Val | Pro | Pro | Gln | Ser | Val | Thr | Ile | |
| | | | 180 | | | | | 185 | | | | | 190 | | | |
| GCT | GGC | AGA | TTT | CAG | AAT | ATA | GAA | GCG | GGT | CTG | GCT | GTT | GAG | TAT | CAT | 624 |
| Ala | Gly | Arg | Phe | Gln | Asn | Ile | Glu | Ala | Gly | Leu | Ala | Val | Glu | Tyr | His | |
| | | 195 | | | | | 200 | | | | | 205 | | | | |
| GCT | GTA | CAG | GTT | TCC | TGG | AGT | GCC | GGT | ACC | ACC | AAA | GGG | GGA | TAT | ATT | 672 |
| Ala | Val | Gln | Val | Ser | Trp | Ser | Ala | Gly | Thr | Thr | Lys | Gly | Gly | Tyr | Ile | |
| | 210 | | | | | 215 | | | | | 220 | | | | | |
| TCC | AAT | CGT | CGG | TTC | ACT | GAC | ATT | TGT | ATC | CTG | AGC | CTT | AAG | ATC | CAG | 720 |
| Ser | Asn | Arg | Arg | Phe | Thr | Asp | Ile | Cys | Ile | Leu | Ser | Leu | Lys | Ile | Gln | |
| 225 | | | | | 230 | | | | | 235 | | | | | 240 | |
| TAA | | | | | | | | | | | | | | | | 723 |
| * | | | | | | | | | | | | | | | | |

What is claimed is:

1. An isolated DNA molecule encoding ShET1 which consists of the amino acid sequence encoded by the DNA of SEQ ID NO:15.

2. The isolated DNA molecule of claim 1, wherein said DNA molecule consists of the nucleotide sequence shown in SEQ ID NO:15.

3. A mutant *Shigella flexneri* 2*a* which fails to produce any enterotoxic ShET1, ShET2 or both, as a result of a mutation in the ShET1, ShET2 or both genes.

4. The mutant *Shigella flexneri* 2*a* of claim 3, wherein said mutation is a deletion mutation.

5. The mutant *Shigella flexneri* 2*a* of claim 4, wherein said mutant has an aro$^-$ and VirG$^-$ phenotype.

6. The mutant *Shigella flexneri* 2*a* of claim 3, wherein said mutation is introduced into parent strain *Shigella flexneri* 2*a* strain CVD1203 (ATCC NO. 55556).

7. A plasmid comprising the DNA of claim 1.

8. A plasmid comprising the DNA of claim 2.

* * * * *

UNITED STATES PATENT AND TRADEMARK OFFICE

CERTIFICATE OF CORRECTION

PATENT NO. : 5,589,380 Page 1 of 1
APPLICATION NO. : 08/351147
DATED : December 31, 1996
INVENTOR(S) : Alessio Fasano et al.

It is certified that error appears in the above-identified patent and that said Letters Patent is hereby corrected as shown below:

Insert at Column 1, line 14 the heading --STATEMENT REGARDING FEDERALLY SPONSORED RESEARCH OR DEVELOPMENT--

Insert at Column 1, line 4 following the above heading --This invention was made with the government support under NIH Grant No. AI019716 awarded by the National Insititutes of Health. The government has certain rights in the invention.--

Signed and Sealed this

Eleventh Day of March, 2008

JON W. DUDAS
*Director of the United States Patent and Trademark Office*